United States Patent [19]
Nicolaou et al.

[11] Patent Number: 5,264,586
[45] Date of Patent: Nov. 23, 1993

[54] ANALOGS OF CALICHEAMICIN GAMMA1I, METHOD OF MAKING AND USING THE SAME

[75] Inventors: Kyriacos C. Nicolaou, La Jolla; Adrian L. Smith; Chan-Kou Hwang, both of San Diego; Emmanuel Pitsinos, La Jolla, all of Calif.

[73] Assignee: The Scripps Research Institute, La Jolla, Calif.

[21] Appl. No.: 915,071

[22] Filed: Jul. 16, 1992

Related U.S. Application Data

[63] Continuation-in-part of Ser. No. 731,432, Jul. 17, 1991, abandoned.

[51] Int. Cl.$^5$ .......................... C07F 7/18; C07F 7/08; C07D 317/28; A61K 31/40
[52] U.S. Cl. ..................... 548/406; 536/18.1; 544/220; 546/14; 546/290; 546/291; 546/294; 548/110; 548/123; 548/473; 548/548; 549/214; 549/451; 562/498
[58] Field of Search .................. 548/406, 110; 546/14; 544/220; 549/214

[56] References Cited

U.S. PATENT DOCUMENTS

| | | | |
|---|---|---|---|
| 4,079,125 | 3/1978 | Sipos | 424/23 |
| 4,837,206 | 6/1989 | Golik | 514/25 |

FOREIGN PATENT DOCUMENTS 2179649 3/1987 United Kingdom .

OTHER PUBLICATIONS

Schoenen, Tet. Letters 30, 3765-68 (1989).
Lee et al., J. Am. Chem. Soc., 109:3466 (1987).
Golik et al., J. Am. Chem Soc., 109:342 (1987).
Zein et al., Science, 240:1198 (1988).
Zein et al., Science, 244:697 (1989).
Konishi et al., J. Am. Chem. Soc., 112:3715-3716 (1990).
Konishi et al., J. Antibiot., 42:1449-1452 (1989).
Edo et al., Tetrahedron Lett. (1988).
Chin et al., Biochemistry, 27:8106-8114 (1988).
Lee et al., Biochemistry, 28:1019-1026 (1989).
Nicolaou et al., J. Am. Chem. Soc., 110:4866-4868, 7247-7248 (1988).
Cabal et al., J. Am. Chem. Soc., 112:3253 (1990).
Nicolaou et al., J. Am. Chem. Soc., 112:8193-8195 (1990).
Nicolaou et al., J. Am. Chem. Soc., 112:4085-4086 (1990).
Nicolaou et al., J. Am. Chem. Commun., 1275-1277 (1990).
Schmidt, Angew. Chem. Int. Ed., Engl., 25:212 (1986).
Mukaiyama et al., Chem Lett., 431 (1981).
Nicolaou et al., J. Am. Chem. Soc., 106:4189 (1984).
Zenhavi et al., J. Org. Chem., 37:2281 (1972).
Zenhavi et al., J. Org. Chem., 37:2285 (1972).
Ohtsuka et al., J. Am. Chem. Soc., 100:8210 (1978).
Pillai, Synethesis, 1 (1980).
Grundler et al., Carbohydr. Res., 135:203 (1985).
Paulsen et al., Chem. Ber., 114:3102 (1981).
Mantlo et al., J. Org. Chem., 54:2781 (1989).
Nicolaou et al., J. Am. Chem. Soc., 110:7247 (1988).
Haseltine et al., J. Am. Chem. Soc., 111:7638 (1989).
Magnus et al., Tett. Lett., 30(28):3637-3640 (1989).
Magnus et al., J. Chem. Soc., Chem. Commun., 916-919 (1989).
Magnus et al., Tett. Lett., 30(15:1905-1906 (1989).
Magnus et al., J. Am. Chem. Soc., 110:6921-6923 (1988).
Magnus et al., J. Am. Chem. Soc., 110:1626-1628 (1988).
Schreiber et al., J. Am. Chem. Soc., 110:631-633 (1988).
Schreiber et al., Tett. Lett., 30:(4):433-436 (1989).
Kende et al., Tett. Lett., 29(34):4217-4220 (1988).
Golik et al., J. Am. Chem. Soc. 109:3462-3464 (1987).
Lee et al., J. Am. Chem. Soc., 109:3464-3466 (1987).
Kadow et al., Tett. Lett., 30(27):3499-3500 (1989).
Snyder, J. Am. Chem. Soc., 111:7630-7632 (1989).
Tomioka et al., Tett. Lett., 30(7):851-854 (1989).

Primary Examiner—Mark L. Berch
Attorney, Agent, or Firm—Dressler, Goldsmith, Shoe & Milnamow,

[57] ABSTRACT

Chimeric analogs of calicheamicin that include an analog of calicheamicinone linked to an ester or glycoside, (−)-calicheamicinone and its analogs are disclosed.

6 Claims, No Drawings

ANALOGS OF CALICHEAMICIN GAMMA1I, METHOD OF MAKING AND USING THE SAME

This invention was made with government support under Contract CA 46446 awarded by the National Institutes of Health. The government has certain rights in the invention.

CROSS-REFERENCE TO RELATED APPLICATION

This application is a continuation-in-part of Ser. No. 07/731,432, filed Jul. 17, 1991, now abandoned, whose disclosures are incorporated herein by reference.

DESCRIPTION

1. Technical Field

The present invention relates to synthetic analogs of the enediyne antibiotic calicheamicin $\gamma_1^I$, and more specifically to the synthesis of chimeric analogs of calicheamicin that include an analog of calicheamininone linked to an ester or glycoside and to intermediates useful in those syntheses.

2. Background Art

The calicheamicin $\gamma_1^I$ [Lee et al., *J. Am. Chem. Soc.*, 109:3466 (1987)] and esperamicin [Golik et al., *J. Am. Chem. Soc.*, 109:3462 (1987)] families of antibiotics contain a complex bicyclic enediyne allylic trisulfide core structure linked through glycosyl bonds to an oligosaccharide chain. The oligosaccharide portions of each of those molecules contain a number of substituted sugar derivatives, and each of those oligosaccharide portions contains a tetrahydropyran ring that is substituted on the ring both with a sulfur atom and with the oxygen atom of a hydroxylamine group.

The chemical structure of calicheamicin $\gamma_1^I$ (hereinafter referred to as calicheamicin), which contains a more complex oligosaccharide group than an esperamicin, contains four substituted sugar rings and a substituted benzoyl group in the oligosaccharide portion. Those five linked rings are referred to in the art by the letters A through E. The saccharide unit lettered "B" is the before discussed sulfur- and O-hydroxylamine-substituted tetrahydropyran derivative.

The saccharide rings of an esperamicin corresponding to rings "A" and "E" of calicheamicin are substituted similarly, except that the esperamicin ring corresponding to ring E includes an N-isopropyl rather than N-ethyl group. The corresponding "B" ring of an esperamicin contains an S-methyl rather than the S-(saccharide-substituted)-derivatized benzoyl group (C and D rings) of calicheamicin. The structures of esperamicin and some of its derivatives are illustrated in U.S. Pat. No. 4,837,206, whose disclosures are incorporated by reference.

The enediyne-containing (aglycon or core) and carbohydrate portions of calicheamicin and esperamicin appear to carry out different roles in the biological activity of those molecules. Thus, the core portion appears to cleave DNA [Zein et al., *Science*, 240:1198(1988)], whereas the oligosaccharide portion of calicheamicin appears to guide the drug to a double stranded DNA minor groove in which the drug anchors itself on the 5' side of a TCCT sequence, and the core cleaves the DNA. Esperamicins are less sequence specific. [Zein et al., *Science*, 244:697 (1989)].

Studies of the effect on DNA cleavage of derivatization or removal of one or more of the D and E rings of calicheamicin indicate the following: removal of the E ring (amino sugar) provided a drug with the same DNA cleaving specificity as the parent, but having a DNA-cleaving efficiency 2 to 3 orders of magnitude less; acylation of the E ring amine maintained specificity but lowered efficiency; removal of the D ring (terminal rhamnose) maintained specificity, but lowered efficiency 50-100 times; and removal of the D and E rings (terminal rhamnose and amino sugar) resulted in inhibition of cutting. [Zein et al., *Science*, 244:697 (1989)].

Esperamicin lacks the C and D rings and includes a further complex saccharide structure linked to an additional core hydroxyl group. U.K. Patent Application 2,179,649A reports that acid hydrolysis of esperamicins led to cleavage of that second complex saccharide structure and a resulting esperamicin derivative referred to as BBM-1675C that was about as effective as the starting esperamicin BBM-1675A$_1$ (esperamicin A$_1$), and more so that esperamicin BBM-1675A$_2$ (esperamicin A$_2$) as an antitumor and antimicrobial agent. From the discussion in this U.K. application, the oligosaccharide portion of BBM-1675C contains ring analogous to the A, B and E rings of calicheamicin.

U.K. Patent Application 2,179,649A also disclosed that further hydrolysis of esperamicin BBM-1675C led to another esperamicin derivative named BBM-1675D that was also said to be about as effective as esperamicin BBM-1675A$_1$, as an antitumor and antimicrobial agent. The data presented indicate that esperamicin BBM-1675D possessed only two saccharide rings; i.e. those corresponding to the A and E rings of calicheamicin.

Thus, the art has recognized the importance of the oligosaccharide portions of the calicheamicin and esperamicin antibiotics, and has recognized that the saccharide rings in the calicheamicin group can affect the activity of the drug. The results disclosed in Zein et al., *Science*, 244:697 (1989) and those in U.K. Patent Application 2,179,649A indicate a possible conflict as to the effect of the individual saccharide portions on efficacy, although different assay methods were used.

In addition to calicheamicin and esperamicin, at least two other naturally occurring antibacterial and anticancer, enediyne epoxide compounds have been reported. One, named dynemicin A, was isolated from *Micromonospora chersina* [Konishi et al., *J. Am. Chem. Soc.*, 112:3715–3716 (1990); Konishi et al., *J. Antibiot.*, 42:1449–1452 (1989)]. The second is neocarzinostatin [Edo et al., *Tetrahedron Lett.*, Chin et al., *Biochemistry*, 27:8106–8114 (1988); and the citations therein]. Dynemicin A has no oligosaccharide portion, whereas neocarzinostatin has a pendent 2,6-dideoxy-2-(methylamino)galactosyl group, a 2-hydroxy-5-methoxy-7-methyl-naphthoate group and a 5-membered ring carbonate. Neocarzinostatin exhibits sequence-specificity in its DNA cleavage [Lee et al., *Biochemistry*, 28:1019–1026 (1989).

A number of synthetic enediyne compounds that undergo Bergman-type cyclizations and/or cleave DNA have also been reported. See, for example, Nicolaou et al., *J. Am. Chem. Soc.*, 110:4866–4868, and 7247–7248 (1988).

Thus, it appears as though the oligosaccharide portion of the molecule may assist in site direction for cleavage, but is not required for an enediyne or epoxy enediyne to cleave DNA strands.

Calicheamicin and esperamicin are extremely potent. For example, Zein et al., *Science*, 240:1198–1201 (1988) report calicheamicin to be about 1000-fold more active than adriamycin against murine tumors and to be optimal at about 0.5–1.5 microgram (μg) per kilogram (kg) of body weight. U.K. Application 2,179,649 reports its esperamicin derivatives to have activities at about the same concentrations, with several derivatives being toxic at milligram (mg) to about 0.13 mg/kg levels. Thus, the known derivatives can be too toxic.

It would therefore be of importance to prepare analogs of calicheamicin or esperamicin that are effective, but not as toxic. It would also be of importance to prepare analogs of calicheamicin or esperamicin with oligosaccharide or analogous portions different from the natural oligosaccharide so that the specificity of the drugs can be altered.

The calicheamicin aglycon (calicheamicinone) is one starting point for the preparation of desirable analogs. The synthesis of the racemic (±) calicheamicinone has recently been reported by the Danishefsky group [Cabal et al., *J. Am. Chem. Soc.*, 112:3253 (1990); Haseltine et al., Ibid., 113:3850–3866 (1991)]. An enantioselective total synthesis of (−)-calicheamicinone by a different approach is discussed hereinafter.

The oligosaccharide fragment of calicheamicin is another starting point for the synthesis of desirable analogs. The total synthesis of that oligosaccharide fragment is described in Nicolaou et al., *J. Am. Chem. Soc.*, 112:8193–8195 (1990), with the syntheses of portions of the oligosaccharide being described in Nicolaou et al., *J. Am. Chem. Soc.*, 112:4085–4086 (1990) and Nicolaou et al., *J. Chem. Soc., Chem. Commun.*, 1275–1277 (1990).

BRIEF SUMMARY OF THE INVENTION

The present invention contemplates chimeric analogs of calicheamicin as well as methods of making and using the same. Each chimer is comprised of an aglycone and an oligosaccharide portion.

A compound of the invention corresponds in srstructure to Formula I

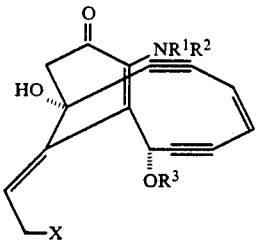

wherein
R$^1$ is hydrogen;
R$^2$ is selected from the group consisting of C$_1$–C$_6$ acyl, benzoyl, C$_1$–C$_6$ alkoxy carbonyl and benzyloxy carbonyl; or
R$^1$ and R$^2$ together form a moiety selected from the group consisting of

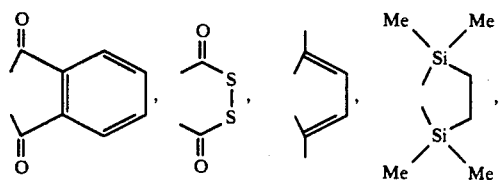

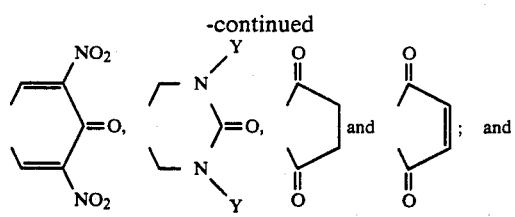

where
Y is methyl or benzyl;
X is OR$^4$, SR$^4$, SSSCH$_3$, SSCH$_3$ or NHR$^4$, where R$^4$ is selected from the group consisting of hydrogen, C$_1$–C$_6$ acyl, benzoyl, and C(O)ZR$^5$, wherein Z is O or NH and R$^5$ is selected from the group consisting of C$_1$–C$_6$ alkyl or benzyl, 3-(phenylsulfonyl)ethyl, 4-(phenylsulfonyl)but-2-enyl; and
R$^3$ is selected from the group consisting of hydrogen, C$_1$–C$_6$ acyl, benzoyl, and a glycosidically linked saccharide moiety selected from the group consisting of ribosyl, deoxyribosyl, glucosyl, galactosyl, N-acetylglucosyl, N-acetylgalactosyl, and a saccharide having a following structure in which the wavy line adjacent a bond indicates the glycosidic linkage

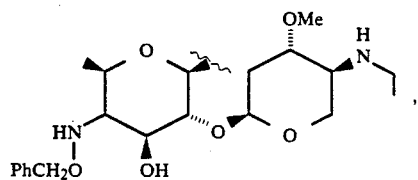

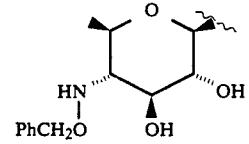

and

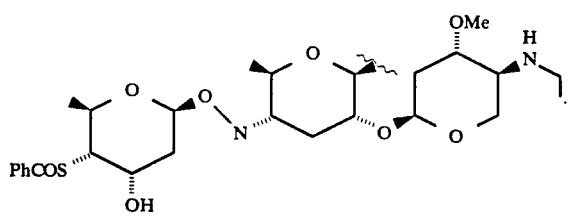

In particularly preferred embodiments, R$^1$ and R$^2$ together with the bonded nitrogen atom (NR$^1$R$^2$) form a phthalimidoyl group, or R$^1$ is hydrogen and R$^2$ is C$_1$–C$_6$ alkoxy carbonyl, preferably methoxy carbonyl. The X group is OH, SH, SSSCH$_3$, S-acetyl or 2-(phenylsulfonyl)ethoxycarbonyloxy (PhSO$_2$CH$_2$CH$_2$OCO$_2$—, where Ph is phenyl). Preferred R$^3$ moieties are hydrogen or one of the three substituted hydroxyl amine-containing saccharides shown above.

A pharmaceutical composition is also contemplated. Such a composition comprises a before-described compound of Formula I, particularly (−)-calicheamicinone or a chimeric compound as active agent dissolved or dispersed in an effective amount in a pharmaceutically acceptable carrier.

Also contemplated are intermediates useful in the preparation of calicheamicinone and its analogs. Particularly preferred intermediates have the individual formulas shown below.

(II)

(III)

wherein
R¹ is hydrogen;
R² is selected from the group consisting of $C_1$-$C_6$ acyl, benzoyl, $C_1$-$C_6$ alkoxy carbonyl and benzyloxy carbonyl; or
R¹ and R² together form a moiety selected from the group consisting of wherein
Y is methyl or benzyl; and
$SiR_3$ contains three R groups that are the same or different and are selected from the group consisting of $C_1$-$C_6$ alkyl and phenyl.

(10)

-continued (IV)

(V)

wherein
MEM is 2-methoxyethoxymethyl, Ac is acetyl and Me is methyl,
R⁶ is $C_1$-$C_6$ acyl or benzoyl,
R⁷ is $C_1$-$C_6$ alkyl, and
$SiR_3$ is as discussed before.

DETAILED DESCRIPTION OF THE INVENTION

I. The Compounds

A compound of the invention has a structure that corresponds to Formula I (I)

wherein
R¹ is hydrogen;
R² is selected from the group consisting of $C_1$-$C_6$ acyl, benzoyl, $C_1$-$C_6$ alkoxy carbonyl and benzyloxy carbonyl; or
R¹ and R² together form a moiety selected from the group consisting of where Y is methyl or benzyl;

X is $OR^4$, $SR^4$, $SSSCH_3$, $SSCH_3$ or $NHR^4$, where $R^4$ is selected from the group consisting of hydrogen, $C_1$-$C_6$ acyl, benzoyl, and $C(O)ZR^5$, wherein Z is O or NH and $R^5$ is selected from the group consisting of $C_1$-$C_6$ alkyl, benzyl, 2-(phenylsulfonyl)ethyl and 4-(phenylsulfonyl)but-2-enyl; and $R^3$ is selected from the group consisting of hydrogen, $C_1$-$C_6$ acyl, benzoyl, and a glycosidically linked saccharide moiety selected from the group consisting of ribosyl, deoxyribosyl, glucosyl, galactosyl, N-acetylglucosyl, N-acetylgalactosyl, and a saccharide having a following structure in which the wavy line adjacent a bond indicates the glycosidic linkage

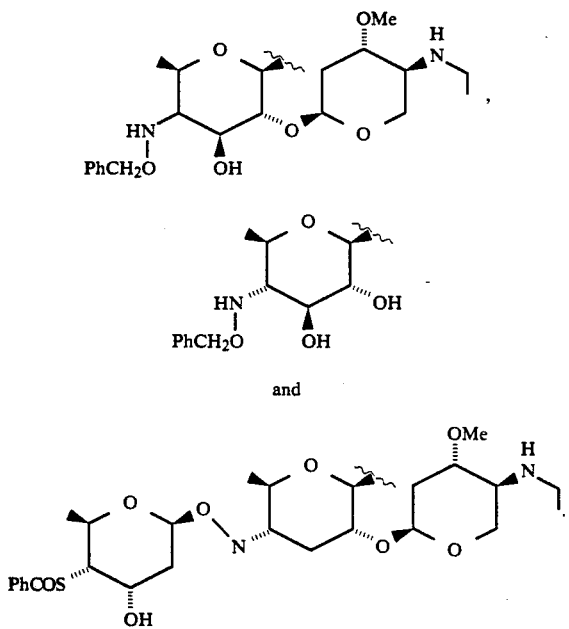

In accordance with one embodiment of the above formula, $R^1$ is hydrogen and $NHR^2$ is an amide or a carbamate. One contemplated amide is a benzoylamide so that $R^2$ is benzoyl. Another contemplated amide is a $C_1$-$C_6$ acyl amide such as an amide of formic, acetic, propionic, butyric, iso-butyric (2-methylpropionic), pentanoic, 3-methylbutyric, hexanoic and the like acids. Thus, an $R^2$ group for those acids can be a formyl, acetyl, propionyl, butyryl, iso-butyryl, pentanoyl, 3-methylbutyryl, hexanoyl or like group. When $NHR^2$ is a carbamate, $R^2$ can be a benzyloxy carbonyl group or a $C_1$-$C_6$ alkoxy carbonyl. Exemplary $C_1$-$C_6$ alkoxy groups are oxy substituted $C_1$-$C_6$ alkyl groups such as methoxy, ethoxy, propoxy, iso-propoxy, butoxy, 2-butoxy, t-butoxy, 2-methylpropoxy, pentyloxy, 2-methylpentyloxy, hexyloxy and the like.

$R^1$ and $R^2$ also, together with the bonded nitrogen, form a cyclic compound such as an imide or a cyclic amino silane and the like as are disclosed above. Preferably, $NR^1R^2$ forms a carbamate, such as the methyl carbamate, or $NR^1R^2$ together form a phthalimido group.

An X group can be a hydroxyl, mercaptan or amine group where $R^4$ is hydrogen. An $R^4$ group can also be a $C_1$-$C_6$ acyl or benzoyl group as discussed previously.

An $R^4$ group can also have the structure $C(O)ZR^5$ so that X is a carbonate, urethan, urea, or isothiourea compound, depending on whether X is $OR^4$, $SR^4$ or $NHR^4$, as well as whether Z is O or NH. A carbonate is preferred in some embodiments so that X has the structure $OC(O)OR^5$. X is $SSCH_3$ or $SSSCH_3$ in another preferred embodiment.

$R^5$ can be a $C_1$-$C_6$ alkyl group in any of those structures. $R^5$ can also be a 2-(phenylsulfonyl)ethyl or 4-(phenylsulfonyl)but-2-enyl group. These groups are typically prepared from the corresponding thiophenyl ethyl carbonate compounds by oxidation with at least two moles of a peroxide-type oxidant such as m-chloroperbenzoic acid. The phenylsulfonyl-containing $R^5$ groups, and particularly the resulting 2-(phenylsulfonyl)ethoxy carbonyloxy group; X; i.e., $X=OR^4$, where $R^4=C(O)OCH_2CH_2SO_2Ph$, are particularly preferred.

An $R^3$ group can be hydrogen, a $C_1$-$C_6$ acyl or benzoyl group as discussed previously in regard to an $R^2$ group. More preferably, in one embodiment, $R^3$ is a glycosidically linked saccharide moiety. Exemplary saccharides include ribosyl, deoxyribosyl, glucosyl, N-acetylglucosyl, galactosyl, N-acetylgalactosyl and the three saccharide units whose structures are shown above.

The three depicted saccharide units correspond to fragments of the calicheamicin oligosaccharide. Thus, the disaccharide corresponds to the calicheamicin A and E rings with the hydroxylamine link to a B ring analog, the monosaccharide corresponds to the A ring alone with the hydroxylamine-linked B ring analog, and the trisaccharide thiobenzoate corresponds to rings A, E and B, and a C ring analog. These saccharides are discussed in more detail hereinafter.

A compound of Formula I is (−)-calicheamicinone, Compound 2, when $R^1$ is hydrogen, $R^2$ is methoxycarbonyl, $R^3$ is hydrogen and X is $SSSCH_3$. Two syntheses are illustrated hereinafter for Compound 2. (−)-Calicheamicinone is the aglycone of calicheamicin $\gamma_1^I$. Data provided hereinafter illustrate that Compound 2 exhibits in vitro activity against a number of cancer cell lines that is similar to that exhibited by daunomycin, a well known anticancer antibiotic.

In view of the complexity of the aglycon and oligosaccharide portions of a chimeric compound of the invention, those two portions will be discussed separately hereinbelow.

A. The Aglycon

In one embodiment, an aglycon useful herein has a structure that is similar to that of calicheamicinone, but lacks, inter alia, the trisulfide portion of that molecule. In another embodiment, the aglycone includes that trisulfide ($SSSCH_3$) and is the aglycone of calicheamicin $\gamma_1^I$. Some of the intermediates described by the Danishefsky group such as Compounds 108, 109 and 111 described in Haseltine et al., J. Am. Chem. Soc., 113;3850–3866 (1991) can be used herein.

However, a new enantiospecific syntheses of (−)-calicheamicinone has been devised, and intermediates prepared in accordance with that synthesis are thought to be more amenable to synthesis of calicheamicinone and its analogs, as well as the chimeric analogs desired herein. Those syntheses are outlined in Schemes 1–6 hereinbelow.

Scheme 1

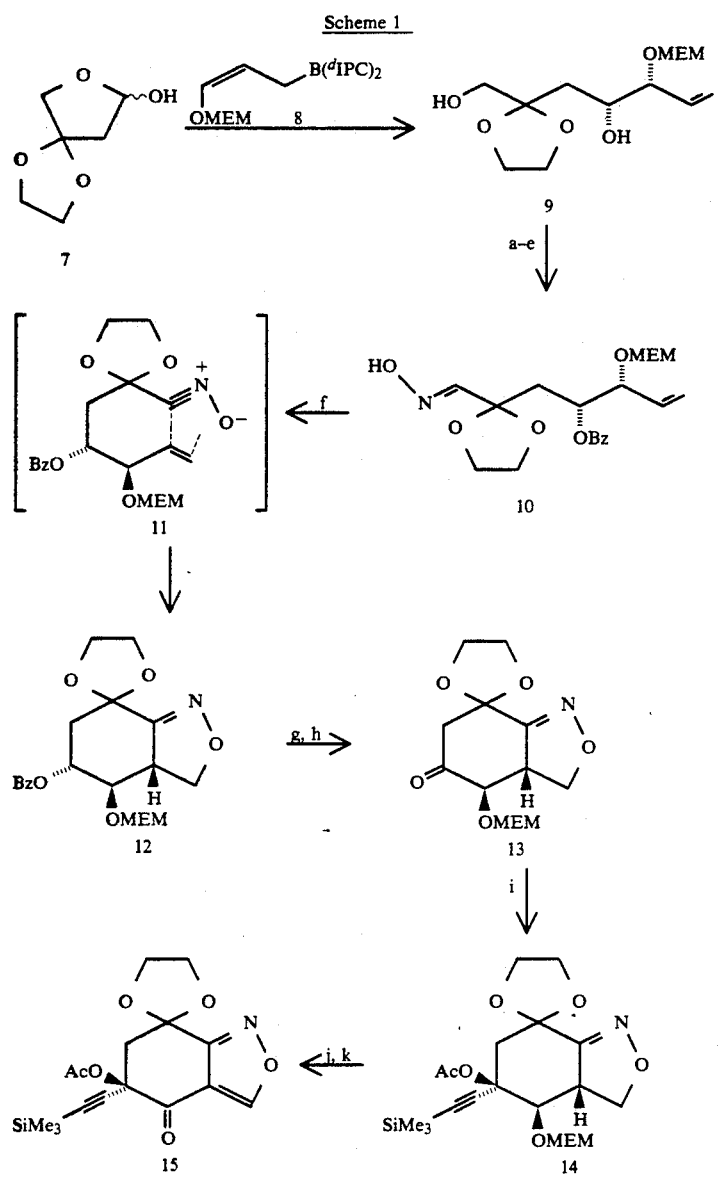

Turning first to Scheme 1, lactol Compound 7, readily prepared from tetronic acid via ketalisation (ethylene glycol, p-toluenesulfonic acid heated in benzene to give a 70 percent yield) and DIBAL reduction (84 percent), was treated with the allyl borane Compound 8 according to the general procedure reported by Brown et al., *J. Am. Chem. Soc.*, 110:1535 (1988) to give Compound 9 in a highly stereo- and enantioselective manner (95 percent ee). Compound 9 was converted to aldoxime Compound 10 in 86 percent overall yield by the following sequence using steps a-e as follows: (i) selective silylation at the primary position using one equivalent of t-butyldimethylsilyl chloride ($^t$BuMe$_2$SiCl) and imidazole, step a; (ii) benzoylation at the secondary position using benzoyl chloride in pyridine plus 4-dimethylaminopyridine (DMAP), step b; (iii) desilylation with the tetra-N-butylammonium fluoride ($^n$Bu$_4$NF) in THF, step c; (iv) Swern oxidation, step d; and (v) oxime formation using hydroxylamine hydrochloride and sodium acetate in ethanol-water, step e. Generation of the nitrile oxide intermediate, Compound 11, by treatment of Compound 10 with aqueous sodium hypochloride in methylene chloride for two hours at zero degrees C. was followed by spontaneous cyclization resulting in a 4:1 mixture of isoxazoline disastereoisomers (65 percent combined yield) from which the major isomer Compound 12 was isolated by flash chromatography in step g.

Debenzoylation of Compound 12 (step g), followed by Jones oxidation using 1.5 equivalents of Jones reagent at zero degrees C. (step h), then afforded ketone Compound 13 in 95 percent overall yield. Addition of Compound 13 to lithium trimethylsilylacetylide at −78° C. proceeded with complete stereoselectivity delivering the incoming nucleophile from the opposite side of the —OMEM group to give, after quenching with acetic anhydride at −78° C.→25° C., acetate Compound 14 (78 percent overall yield) in step i. Removal of the MEM group in step j with zinc bromide followed by Swern oxidation (step k) resulted in concommitant aromatization to give the keto isoxazole Compound 15 in 54 percent overall yield.

Scheme 2

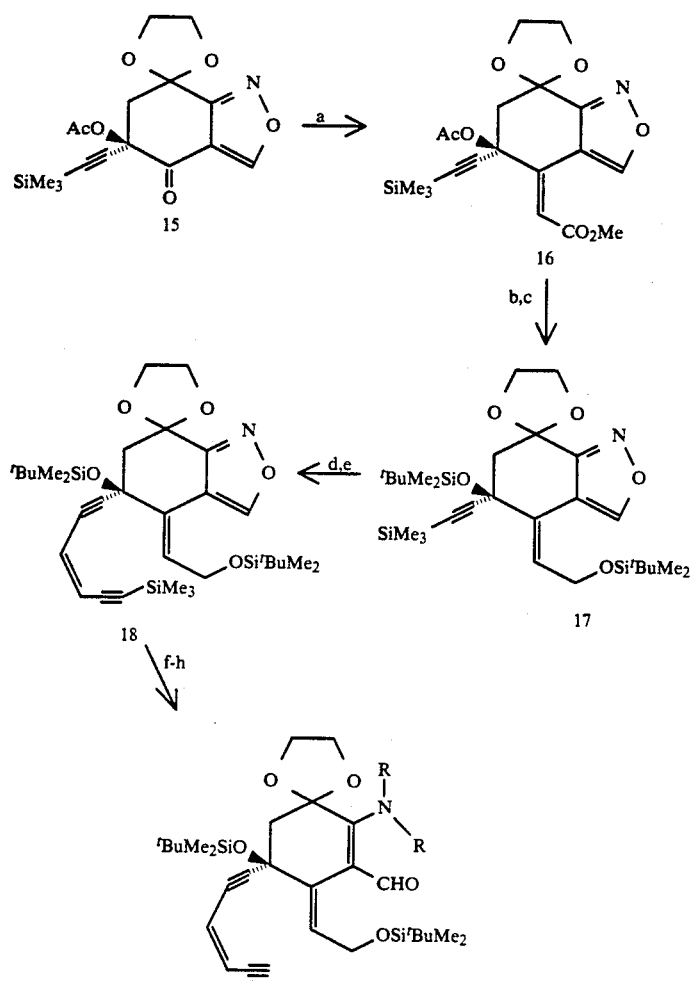

19: R,R = H₂
20: R,R = Phthaloyl
       (Phth)

Turning now to Scheme 2, stereocontrolled olefination of Compound 15 proceeded smoothly upon heating with methyl triphenylphosphoranylidene acetate in toluene at 90° C. for 16 hours to afford solely the desired geometrical isomer of the conjugated methyl ester Compound 16 in 87 percent yield in step a. DIBAL-induced reduction (4 equivalents) in CH$_2$Cl$_2$ at $-78° \rightarrow 0°$ C. of the ester functionality and concommitant removal of the acetate group in step b, followed by persilylation using t-butyldimethylsilyl triflate ($^t$BuMe$_2$. SiOTf) and 2,6-lutidine gave the bis(silyl)ether Compound 17 in 82 percent overall yield in step c. Liberation of the terminal acetylenic group in step d using lithium hydroxide in THF-water in step d, followed by palladium (0)-catalyzed coupling with cis-vinyl chloride trimethylsilylacetylene using a catalytic amount of CuI and n-butylamine in benzene in step e gave, in 68 percent overall yield, the enediyne system Compound 18.

Opening of the isoxazole ring with molybdenum hexacarbonyl [Nitta et al., *J. Am. Chem. Soc.*, 104:877 (1982); one equivalent in acetonitrile:water (20:1)] at 80° C. for 16 hours in step f, followed by lithium hydroxide-induced desilyation of the terminal acetylene in THF-H$_2$O as step g, resulted in the formation of the vinylogous formamide Compound 19 in 60 percent overall yield. Due to the propensity of the aldehyde function to enolize utilizing the nitrogen-bound protons, it was necessary at this stage to protect the nitrogen functionality with a group that removed both of those protons. Thus the phthalimido derivative Compound 20 was prepared in step h by treatment of Compound 19 with phthaloyl dichloride in pyridine-dichloromethane (70 percent yield) setting the stage for the crucial cyclization steps that are shown in Scheme 3.

Scheme 3

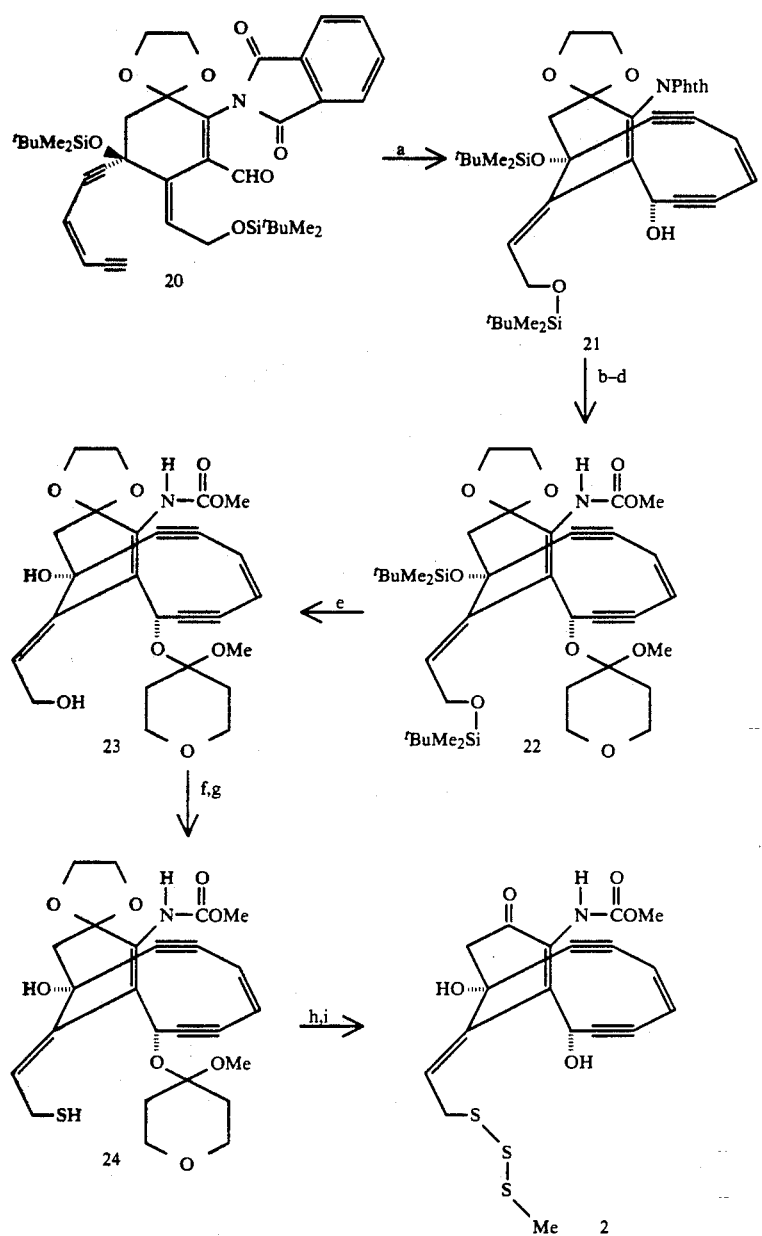

Scheme 3 outlines the final steps of the total synthesis of calicheamicinone, Compound 2, following modifications of the reactions reported by Danishefsky et al. [Cabal et al., *J. Am. Chem. Soc.*, 112:3253 (1990); Haseltine et al., *J. Am. Chem. Soc.*, 113:3850 (1991)]. Thus, ring closure of Compound 20 under basic conditions using KN(SiMe$_3$)$_2$ in toluene at −78° C. in step a proceeded exceptionally well to afford stereospecifically Compound 21 (50 percent yield), which was protected as the methoxytetrahydropyranyl derivative by reaction with 5,6-dihydro-4-methoxy-2H-pyran and acid in step b (85 percent yield). Deprotection of the primary amine with hydrazine (step c), followed by installment of the urethane moiety under standard conditions (methylchloroformate and base) in step d gave Compound 22. Desilylation with $^n$Bu$_4$NF (step e), gave Compound 23. Introduction of the thioacetate group by a Mitsunobu reaction (thioacetic acid, triphenylphosphine and diethyl azodicarboxylate) in step f, followed by treatment with DIBAL generated the thiol Compound 24 in step g. Compound 24 was treated with methylphthalimidodisulfide. A SSCH$_3$ group can be similarly prepared using methylphthalimidodisulfide. Deprotection with camphorsulfonic acid (CSA) led to (−)-calicheamicinone, Compound 2 in 42 percent overall yield.

Each of the above new compounds exhibited satisfactory spectral and analytical data and/or exact mass spectral data. Yields refer to spectroscopically or chromatographically homogeneous materials. Analytical data for Compound 21 are provided hereinafter.

Another, more preferred synthesis is illustrated in Schemes 4, 5 and 6 that are shown and discussed below.

Scheme 4

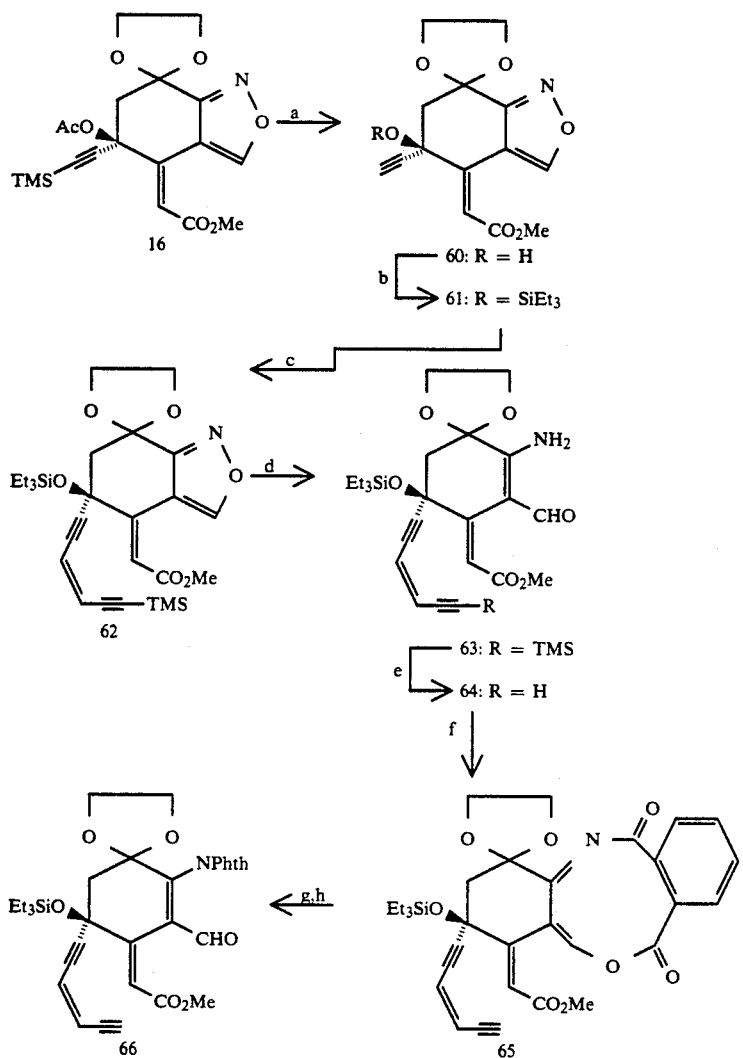

Thus, in Scheme 4, double deprotection of Compound 16 in step a [K$_2$CO$_3$, MeOH:THF(1:1) at zero degrees C. for 12 hours] gave an 96 percent yield of acetylenic alcohol Compound 60, which was silylated (1.5 equivalents TESOTf, 2.0 equivalents 2,6-lutidine, CH$_2$Cl$_2$ at zero degrees C. for 30 minutes) to give Compound 61 in 97 percent yield in step b. Compound 61 coupled to (Z)-(4-chloro-3-buten-1-ynyl)trimethylsilane [0.07 equivalents Pd (O)-0.2 equivalents Cu (I) catalysis, 1.5 equivalents of $^n$BuNH$_2$ in benzene at zero degrees C.][Stephens et al., *J. Org. Chem,* 28:3313 (1963); Ratovelomanana et al., *Tetrahedron Lett.,* 22:315 (1981); Guillerm et al., *Tetrahedron Lett.,* 26:3811 (1985)] to give a 91 percent yield of enediyne Compound 62 after two hours as step c. Hydrogenolytic cleavage of the isooxazole with molybdenum hexacarbonyl [Nitta et al., *J. Chem. Soc., Chem. Commun,* 877 (1982)][MeCN-H$_2$O (5:1), 80° C., 1.5 hours] then gave a 80 percent yield of vinylogous amide Compound 63 in step d, from which the TMS group was removed (as in step a) in 92 percent yield providing the unprotected enediyne Compound 64.

Reinvestigation of the phthaloylation reaction withn phthaloyl chloride/pyridine (1.4 equivalents phthaloyl chloride, 4 equivalents pyridine in MeNO$_2$ at zero degrees C. for 30 minutes) revealed that whilst a minor amount of the required phthalimide Compound 66 was produced in step f, virtually all of the remaining material was accounted for in the formation of the labile, novel 9-membered heterocyle, Compound 65. Fortunately, it was found that hydrolysis of the enol ester on silica gel (CH$_2$Cl$_2$, 25° C., two hours) and activation of the resulinting phthalamic acid with acetic anhydride (excess Ac$_2$O, MeNO$_2$, 25° C., one hour) produced a mixture of the desired phthalimide Compound 66 together with Compound 65. The use of polar solvents such as nitromethane greatly favored N-acylation over O-acylation in this second step so that recycling of Compound 65 twice provided a 78 percent overall yield of phthalimide Compound 66 from Compound 64.

Scheme 5

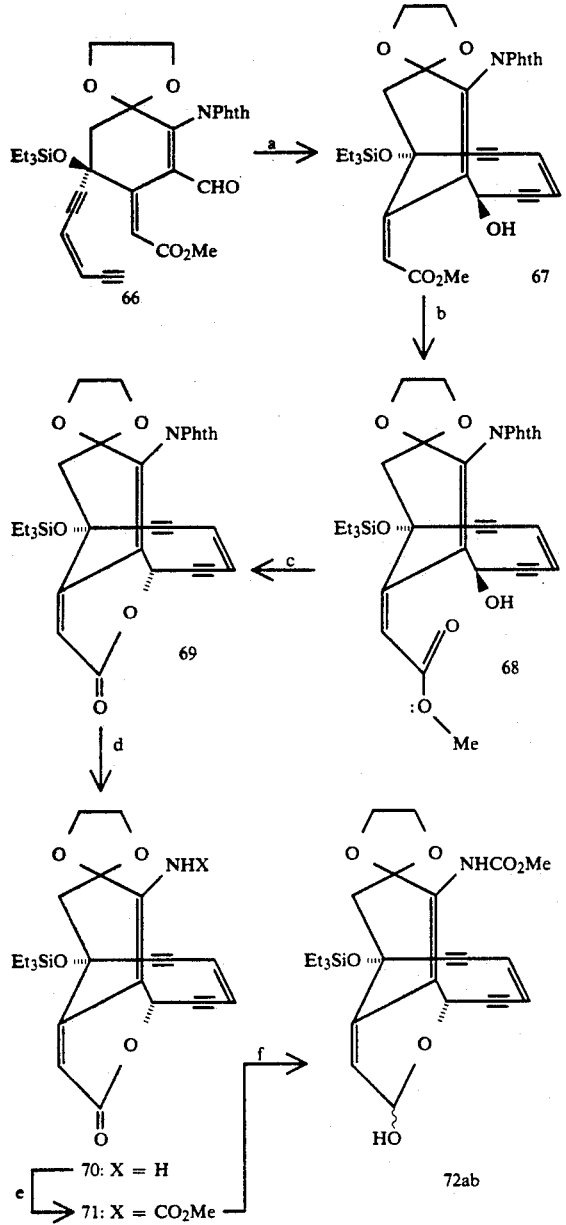

As shown in Scheme 5, treatment of Compound 66 with potassium hexamethyldisilazide (KHMDS; 1.1 equivalents) in toluene at −90° C. produced Compound 67, as step a, contaminated with approximately 10 percent of the free amine in yields of up to 48 percent (56 percent based upon recovered Compound 66). It is noted that the use of freshly prepared reagent [from KH and HN(SiMe₃)₂ in THF] consistently provided slightly better results than the use of a fresh bottle of commercially available reagent, and its was important to quench the reaction at low temperature with acetic acid in order to minimize hydrolysis of the phthalimide by the neighbouring alkoxide anion. The use of other bases in this cyclization reaction was less satisfactory.

The stereochemistry of the newly generated secondary hydroxyl center in Compound 67 was uncertain, but an attempt to install the methyl carbamate unequivocally confirmed that it was of the incorrect stereochemistry for (−)-calicheamicinone. Thus, removal of the phthalimide from Compound 67 with methylhydrazine gave a rather labile enamine. Hydrazine hydrate caused the undesired reduction of the enediyne. Treatment with triphosgene/pyridine followed by MeOH then resulted in the isolation of a cyclic carbamate, a result that would be geometrically impossible for the epimeric alcohol. Thus, the secondary hydroxyl group of Compound 67 had to be inverted.

Whereas the secondary hydroxyl group of Compound 67 was too hindered for traditional intermolecular inversion techniques such as that of Mitsunobu, [Syntheses, 1, (1981)] it was reasoned that since propargylic mesylates have a strong tendency to ionize this might provide an opportunity for the neighbouring ester group to accomplish the inversion in an intramolecular lactonization. Thus, the mesylate (OMs) Compound 68 was prepared from Compound 67 in step b (10 equivalents (MsCl, 20 equivalents pyridine, catalytic DMAP, CH₂Cl₂ zero degrees C., two hours). The proposed lactonization (Compound 68→Compound 69) cleanly took place on a silica gel t.l.c. plate (observed by two-dimensional t.l.c.). On a preparative scale, stirring Compound 68 with a slurry of silica gel in benzene converted it to Compound 69 (step c) but the process was complicated by partial hydrolysis of the silyl ether and ethylene ketal. These side reactions were readily eliminated by the addition of two equivalents of pyridine to neutralize the generated methanesulfonic acid that was the presumed culprit, providing an 90 percent yield of lactone Compound 69 from Compound 67.

Removal of the phthalimide from Compound 69 with methylhydrazine (10 equivalents, benzene, 25° C., 30 minutes) gave an 85 percent yield of the stable enamine Compound 70 in step d, which was converted to the methyl carbamate Compound 71 in 88 percent yield in step e by treatment with triphosgene (3 equivalents)-/pyridine (15 equivalents, CH₂Cl₂, 25° C., 40 minutes followed by MeOH.

Scheme 6

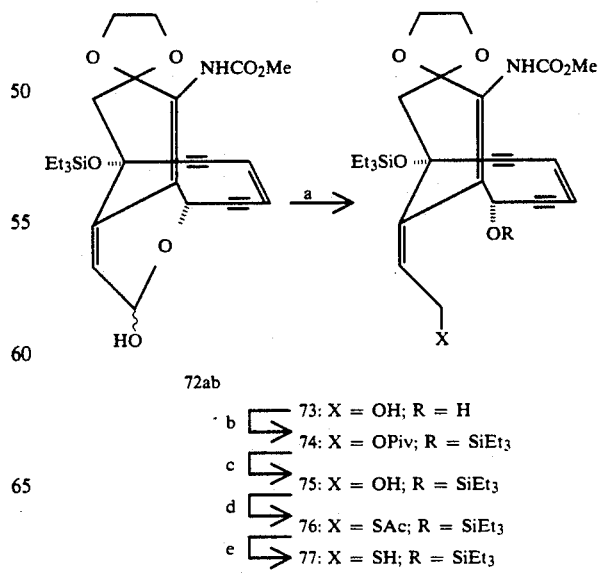

-continued
Scheme 6

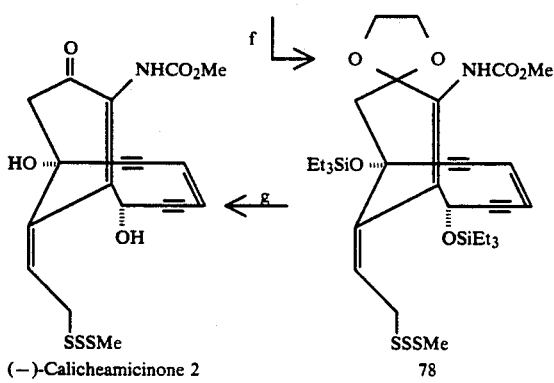

(−)-Calicheamicinone 2      78

The conclusion of the synthesis then followed along the lines of Danishefsky's synthesis of (±)-calicheamicinone. [Cabal et al., *J. Am. Chem. Soc.*, 112:3253 (1990); Haseltine et al., *J. Am. Chem. Soc.*, 113:3850 (1991).] Thus, DIBAL reduction of Compound 71 gave a 4:1 mixture of lactol epimers Compounds 72ab (step f of Scheme 5, 95 percent yield) which were further reduced as shwon in Scheme 6 with NaBH$_4$ to diol Compound 73 (step a, 88 percent yield). Direct introduction of the primary allylic thioacetate group at this stage through a Mitsunobu reaction with thiolacetic acid [Volante, *Tetrahedron Lett.*, 22:3119 (1981)] was badly complicated by intramolecular etherification to give a dihydropyran as the major product in a ratio of about 2:1.

Therefore a diprotection-deprotection sequence (Compounds 73→74→75, steps b and c) was carried out to selectively protect the secondary hydroxyl group in 52 percent overall yield. Mitsunobu reaction with thiolacetic acid [Volante, *Tetrahedron Lett.*, 22:3119 (1981)] then introduced the thioacetate of Compound 76 (step d, 93 percent yield) which was deacylated (DIBAL) to form Compoun 77 in step e, and converted to the trisulfide Compound 78 with N-(methyldithio)phthalimide [Harpp et al., *Int. J. Sulfur Chem. Part A*, 1:57 (1971); Sullivan et al., *Int. J. Sulfur Chem. Part A*, 1:211 (1971)] in 71 percent yield in step f following the methodology developed by Magnus on a model system. [Magnus et al., *J. Chem. Soc., Chem. Commun.*, 916 (1989)].

A final deprotection of the ethylene ketal and two silyl ethers was accomplished in one pot with TsOH in aqueous THF in 66 percent yield in step g, thus completing the asymmetric synthesis of (−)-calicheamicinone, Compound (2). The material thus obtained was spectroscopically identical to the (±)-calicheamicinone previously obtained by Danishefsky, and had a rotation [a]$_D^{25}$ = −472° (c 0.21, CH$_2$Cl$_2$) [estimated weighing error = ±5 percent]. No sample of natural calicheamicinone is available for comparison purposes since it has not been possible to isolate the intact aglycone from degradation studies.

In examining the above synthetic schemes, and particularly Schemes 2 and 3, it is apparent how this synthesis lends itself to the ready preparation of the calicheamicinone as well as calicheamicinone analogs that are of interest herein. Compounds 20 and 21 and their analogs are particularly useful intermediates.

For example, one of the combined R$^1$ and R$^2$ groups noted before can be utilized instead of a phthaloyl group to prepare a derivative other than Compound 20 from Compound 19. That derivative can be maintained throughout the synthesis.

Those other combined R$^1$R$^2$ groups can be prepared by standard techniques as follows.

The dithiasuccinoyl group is prepared by reaction of the free amine first with O-ethyl-S-carboxymethyl dithiocarbonate to form the ethyloxythiocarbonyl derivative, and then with chlorocarbonylsulfonyl chloride. The formed dithiasuccinoyl amine can be removed by reaction with a mercaptan such as β-mercaptoethanol in the presence of triethylamine in dichloromethane. Barany et al., *J. Am. Chem. Soc.*, 99:7363–7365 (1977).

A succinoyl or maleyl group can be similarly prepared by reaction of the anhydride and free amine in DMF-toluene at reflux. Succinyl chloride in pyridine can also be used. Each of the described imide-type R$^1$R$^2$ groups can be removed by reaction with hydrazine, using well known conditions.

The dimethylpyrrole derivative is prepared by reaction of the free amine with acetylacetone and acetic acid. The tetramethyldisilylethylene derivative is prepared from the free amine and 1,1,4,4-tetramethyl-1,4-dichlorodisilylethylene in the presence of a base such as triethylamine. The 2,6-dinitropyridone derivative is prepared by reaction of the free amine with N-(p-nitrophenyl)-2,4-dinitropyridone in pyridine.

A triazone derivative is prepared by reaction of the free amine with the disubstituted urea in aqueous formaldehyde at 70°-100° C., with there being at least two equivalents of formaldehyde present per urea and free amine. This blocking group can be removed by reaction in the presence of saturated aqueous ammonium chloride at 70° C. Knapp et al., *Tetrahedron Lett.*, 31:2109–2112 (1990).

In addition, an R$^2$ C$_1$–C$_6$ acyl, benzoyl, C$_1$–C$_6$ alkoxy carbonyl or benzyloxy carbonyl group other than the methoxy carbonyl introduced at step d of Scheme 3 can be added at that step to the free amine generated in step c. Of course, the combined R$^1$ and R$^2$ groups can also be introduced at step d of Scheme 3 instead of the urethane group shown.

An X=OR$^4$ group where R$^4$ is hydrogen is formed in step e of Scheme 3. An X=SR$^4$ group where R$^4$ is hydrogen is formed in step g. The remaining OR$^4$ and SR$^4$ derivatives can be prepared from those intermediates by acylation using an appropriate acid halide or N-hydroxysuccinimidoyl ester.

It is noted that the sulfone-containing compounds are formed first from corresponding thioethers, which are thereafter oxidized with an excess of peroxide-type oxidant such as m-chloroperbenzoic acid.

It is also noted that a desired "X" group can be added to Compound 23 or 24, and the ketone and secondary, propargyl alcohol thereafter deblocked to provide a compound of Formula I in which R$^3$ is H. That compound can be glycosylated or acylated as discussed hereinafter.

An aglycon portion where X is NH$_2$ or NHR$^4$ can also be prepared from Compound 23 of Scheme 3. Here, the allylic alcohol is converted to its corresponding tosylate or mesylate, and that derivative is reacted with sodium azide in DMF. Treatment of the azido-containing compound with H$_2$S and piperidine in methanol forms the desired allylic amine that can be used alone, but is preferably reacted further to form an NHR$^4$ group as discussed before.

As noted previously, intermediates having the structures of Compounds 20 and 21 and their analogs are particularly useful intermediates in the formation of calicheamicinone. An analog of one of those compounds is a compound having either or both protecting groups on the nitrogen atom and hydroxyls different from those shown for Compounds 20 and 21. Those analogs are generically shown below in Formulas II and III, respectively.

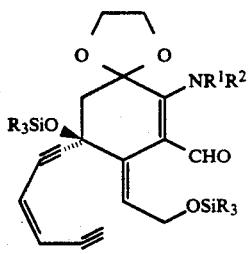
II

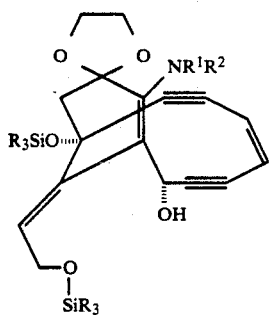
III

In the above formulas, $R^1$ and $R^2$ are as before described, and are preferably one of the depicted groups that form a ring with the nitrogen atom.

An $SiR_3$ group is a silyl-containing protecting group in which each R group is the same or different and is selected from the group consisting of $C_1-C_6$ alkyl and phenyl, each $SiR_3$ group is preferably the same or a $^tBuMe_2Si$ group is used. Thus, the $^tBuMe_2Si$ group of Compounds 20 and 21 are contemplated, as are other well known silyl blocking groups such as trimethylsilyl ($SiMe_3$), triethylsilyl ($Et_3Si$), trihexylsilyl ($SiHex_3$), diphenylmethylsilyl ($Ph_2MeSi$), triphenylsilyl ($Ph_3Si$) and the like.

Compounds 10, 15 and 16 that are intermediates in both described syntheses, and analogs of Compound 15 and 16 shown by Formulas IV and V are also useful and important intermediates. Structural formulas for those compounds are shown below.

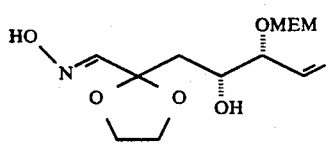
10

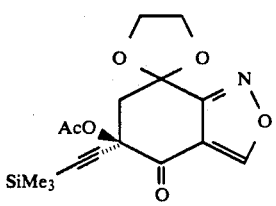
15

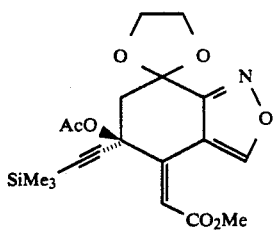
16 wherein MEM is 2-methoxyethoxymethyl, Ac is acetyl and Me is methyl, as are well known by skilled workers.

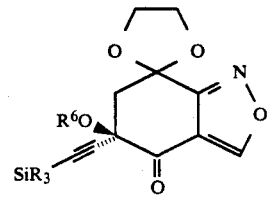
IV

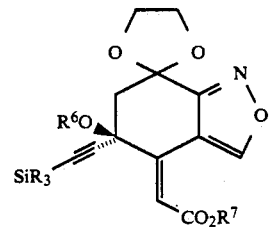
V wherein $R^6$ is $C_1-C_6$ acyl such as acetyl, butanoyl or hexanoyl, or benzoyl, $R^7$ is $C_1-C_6$ alkyl as discussed elsewhere, and $SiR_3$ is as discussed before. In a compound of Formulas IV and V, $R^6$ is preferably acetyl, $SiR_3$ is preferably trimethylsilyl, and $R^7$ is preferably methyl; i.e., Compounds 15 and 16 are preferred specific compounds of Formulas IV and V.

B. The Oligosaccharide

The oligosaccharide portion of a chimer molecule can include a $C_1-C_6$ acyl or benzoyl group, already discussed, which, of course is not an oligosaccharide. However, because those ester groups are in the position normally occupied by an oligosaccharide and can be an $R^3$ group, they are included here and are included in the oligosaccharide portion of the molecule as compared with the aglycon portion.

The oligosaccharide portion of the molecule is typically added after the synthesis of the aglycon portion is complete, except for any blocking groups on otherwise reactive functionalities that are typically removed after addition of the oligosaccharide portion. For the above esters, reaction of a suitably activated acid as discussed before accomplishes the desired result. A sugar moiety is added by standard techniques as are discussed hereinafter.

A monosaccharide moiety such as ribosyl, deoxyribosyl, glucosyl, galactosyl, N-acetylglucosyl, N-acetylgalactosyl or the three saccharides whose structures were shown previously are typically activated prior to linkage to the aglycon.

For example, the 1-position hydroxyl group of an otherwise protected sugar (as with $^tBuMe_2Si$ groups) is reacted with diethylaminosulfur trifluoride (DAST) in THF and in the presence of 4 Å molecular sieves at −78° C. to form the 1-fluoroderivative. The aglycon whose R³ group is hydrogen is then reacted with the 1-fluoro-protected saccharide in the presence of silver perchlorate and stannous chloride to provide a protected desired, typically blocked, chimer molecule.

Similarly, treatment of 1-position hydroxyl of an otherwise protected saccharide with sodium hydride and trichloracetonitrile [Grandler et al., *Carbohydr. Res.*, 135:203 (1985); Schmidt, *Angew. Chem. Int. Ed., Engl.*, 25:212 (1986)] in methylene chloride at about room temperature provides a 1-α-trichloroacetimidate group to activate the saccharide for coupling with the aglycon. Coupling is then carried out with boron trifluoride-etherate in methylene chloride to provide the protected desired chimeric compound.

Once the aglycon and oligosaccharide are coupled, the protecting groups that are present are removed to provide the desired compound, which is then recovered using standard techniques.

Inasmuch as the three depicted saccharides of the calicheamicin oligosaccharide are derivatives of known compounds, as are their suitably protected precursors, their complete syntheses need not be discussed in complete detail herein. Again, those syntheses are described in Nicolaou et al., *J. Am. Chem. Soc.*, 112:4085–4086 (1990); Nicolaou et al, Ibid., 112:8193–8195 (1990); Nicolaou et al., *J. Chem. Soc., Chem. Commun.*, 1275–1277 (1990) as well as in U.S. patent application Ser. No. 07/695,251 filed May 3, 1991, all of whose disclosures are incorporated by reference herein.

The disaccharide-linked hydroxylamine compound is prepared in a manner analogous to that of Compound 12 of Nicolaou et al., *J. Am. Chem. Soc.*, 112:8193–8195 (1990), except that an o-nitrobenzyl (ONB) glycoside is utilized instead of the methyl glycoside precursor, Compound 9, of that paper. The synthesis for the disaccharide is illustrated in Schemes 7 and 8, and is discussed below.

Scheme 7

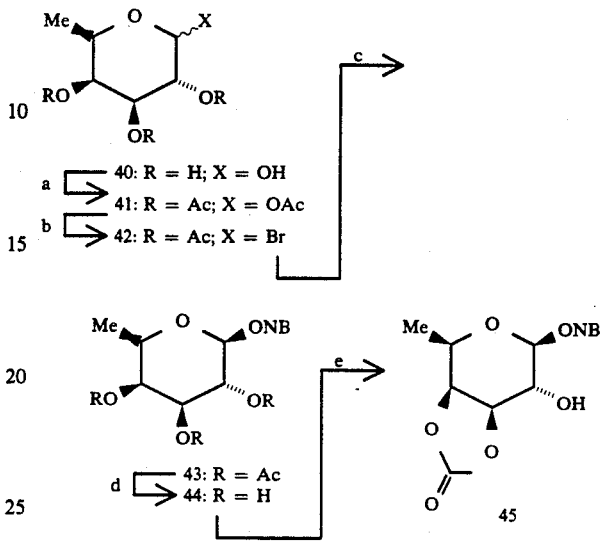

Thus, D-fucose Compound 40 was peracetylated in step a to form tetraacetate Compound 41 which was converted to the anomeric bromide Compound 42 in step b, and glycosylated with o-nitrobenzyl alcohol to afford Compound 43 in step c (63 percent overall yield). Deacetylation of Compound 43 in step d led to Compound 44, which reacted selectively with carbonyl diimidazole in step e to afford the requisite ring A intermediate 45 in 86 percent overall yield.

Scheme 8

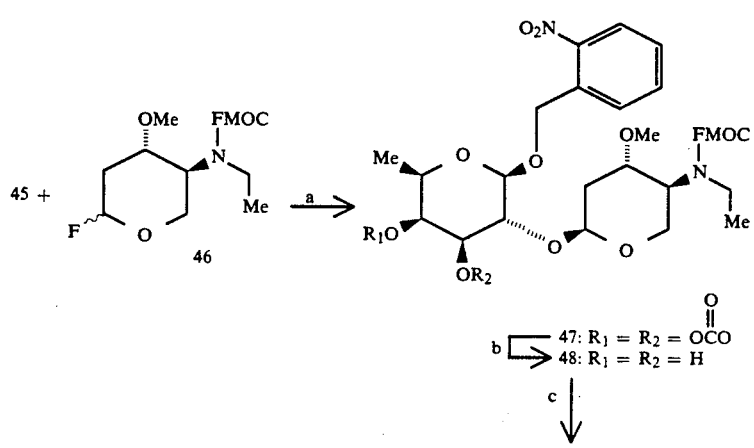

Scheme 8 -continued

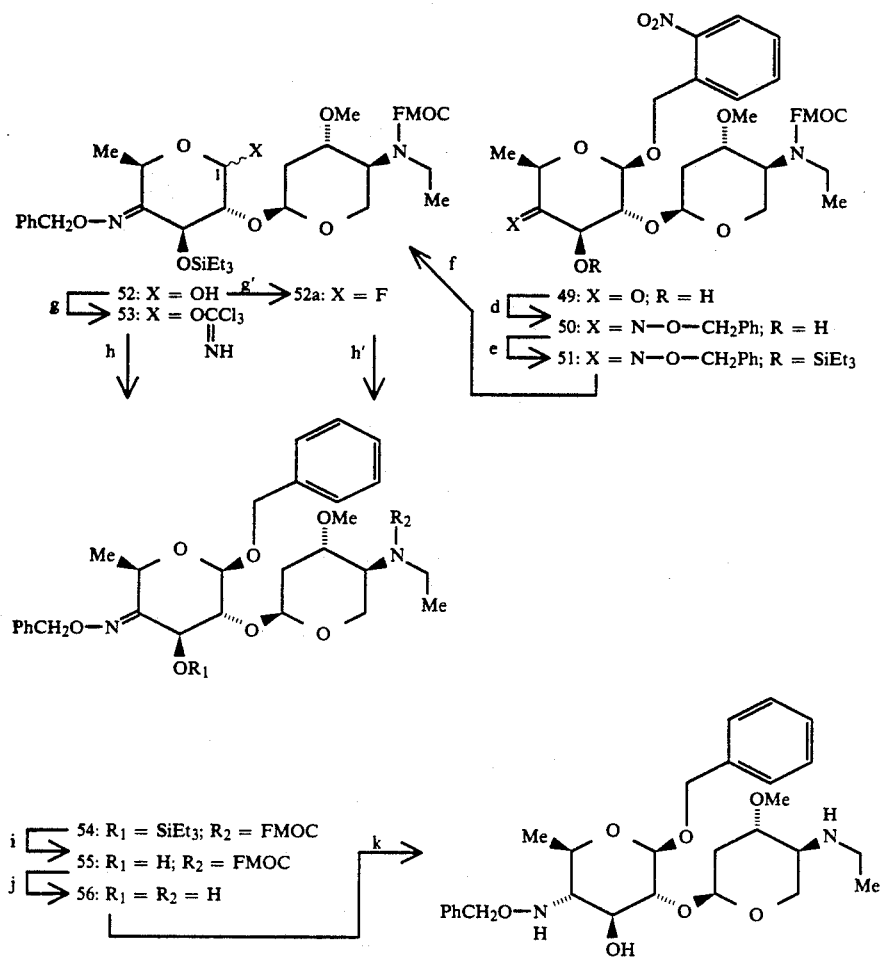

Turning to Scheme 8, intermediate Compound 45 was then coupled [Mukaiyama et al., *Chem. Lett.*, 431 (1981); Nicolaou et al., *J. Am. Chem. Soc.*, 106:4159 (1984)] to glycosyl fluoride Compound 46 (Compound 8 of the above paper; Me=methyl) with $AgClO_4$-$SnCl_2$ catalyst in step a, leading stereoselectively to disaccharide Compound 47 as the major anomer (80 pecent yield, about 5:1 ratio of anomers). Chromatographic purification of Compound 47 with removal of the carbonate protecting group ($NaH$—$HOCH_2CH_2OH$, 90 percent) in step b, and treatment with $^nBu_2SnO$—$Br_2$ [David et al., *J. Chem. Soc. Perkin Trans* 1. 1568 (1979)] led to hydroxyketone Compound 49 (65 percent yield plus 17 percent Compound 48) via intermediate Compound 48, formed in step b.

Oxime formation in step d with O-benzyl hydroxylamine under acid conditions led to Compound 50 (90 percent, single geometrical isomer of unassigned stereochemistry; Ph=phenyl) which was silylated in step e under standard conditions to furnish Compound 51 (90 percent). Photolytic cleavage [Zenhavi et al., *J. Org. Chem.*, 37:2281 (1972); Zenhavi et al., ibid, 37:2285 (1972); Ohtsuka et al., *J. Am. Chem. Soc.*, 100:8210 (1978); Pillai, *Synthesis*, 1 (1980)] of the o-nitrobenzyl group from Compound 51 (THF-$H_2O$, 15 minutes) produced lactol Compound 52 in 95 percent yield in step f. Treatment of Compound 52 with $NaH$—$Cl_3C$-$C\equiv N$ [Grandler et al., *Carbohydr. Res.*, 135:203 (1985); Schmidt, *Angew Chem. Int. Ed., Engl.*, 25:212 (1986)] in $CH_2Cl_2$ for two hours at 25° C. in step g resulted in the formation of the α-trichloroacetimidate Compound 53 in 98 percent yield. Reaction of benzyl alcohol (2.0 equivalents) with trichloroacetimidate Compound 53 under the Schmidt conditions [Grandler et al., *Carbohydr. Res.*, 135:203 (1985); Schmidt, *Angew Chem. Int. Ed., Engl.*, 25:212 (1986)][$BF_3.Et_2O$, $CH_2Cl_2$, $-60° \rightarrow -30°$ C.] resulted in stereoselective formation of the β-glycoside Compound 54 (79 percent yield) together with its anomer (16 percent, separated chromatographically)[$^1$H NMR, 500 MHz, $C_6D_6$, 54: $J_{1,2}=6.5$ Hz, epi-Compound 54: $J_{1,2}=2.4$ Hz].

On the other hand, treatment of lactol Compound 52 with DAST in step g' led to the glycosyl fluoride Compound 52a in 90 percent yield (about 1:1 anomeric mixture). Reaction of Compound 52a with benzyl alcohol in step h' in the presence of silver silicate [Paulsen et al., *Chem. Ber.*, 114:3102 (1981)]—$SnCl_2$ resulted in the formation of the β-glycoside Compound 54 and its anomer in 85 percent (about 1:1 anomeric mixture).

Generation of intermediate Compound 56 via Compound 55 proceeded smoothly under standard deprotection conditions in steps i and j. Finally, exposure of Compound 56 to $Ph_2SiH_2$ in the presence of $Ti(O^iPr)_4$ in step k resulted in the formation of the desired target Compound 57 as the only dedectable product (92 percent yield). Interestingly, reduction of Compound 56 with $NaCNBH_3$—H• led predominantly to the 4-epimer of Compound 57 (90 percent yield). The stereochemical assignments of Compound 57 and epi-57 at C-4 were based on $^1H$ NMR coupling constants [$^1H$ NMR, 500 MHz, $C_6D_6$, 57: $J_{3,4}=9.5$, $J_{4,5}=9.5$ Hz; epi-57: $J_{3,4}=1.9$ Hz, $J_{4,5}=1.5$ Hz].

The hydroxylamine linked A ring derivative can be prepared starting with Compound 9 of Nicolaou et al., *J. Am. Chem. Soc.*, 112:8193–8195 (1990). There, the 2-hydroxyl is blocked with a t-butyldimethylsilyl ($^tBuMe_2Si$) group as before, and the carbonate group removed by reaction of sodium hydride in ethylene glycol-THF at room temperature. The keto group can be prepared by oxidation with dibutylstannic oxide ($Bu_2SnO$) in methanol at 65°. The 3-position hydroxyl is similarly blocked with a $^tBuMe_2Si$ group, and the oxime formed as above.

The trisaccharide plus C ring analog can be readily prepared from Compound 19 of Nicolaou et al., *J. Am. Chem. Soc.*, 112:8193–8195 (1990). Thus, that Compound 19 is reacted with benzoyl chloride in the presence of triethylamine and a catalytic amount of DMAP in methylene chloride to provide the blocked oxime-containing trisaccharide.

C. Chimeras

A compound of Formula I other than where $R^3$ is hydrogen can be viewed as a chimera in that it is composed of two portions, aglycon and oligosaccharide, that are not found together in nature. The following discussion and Schemes 9 and 10 will be used to illustrate preparation of chimeric compounds of the invention.

Scheme 9

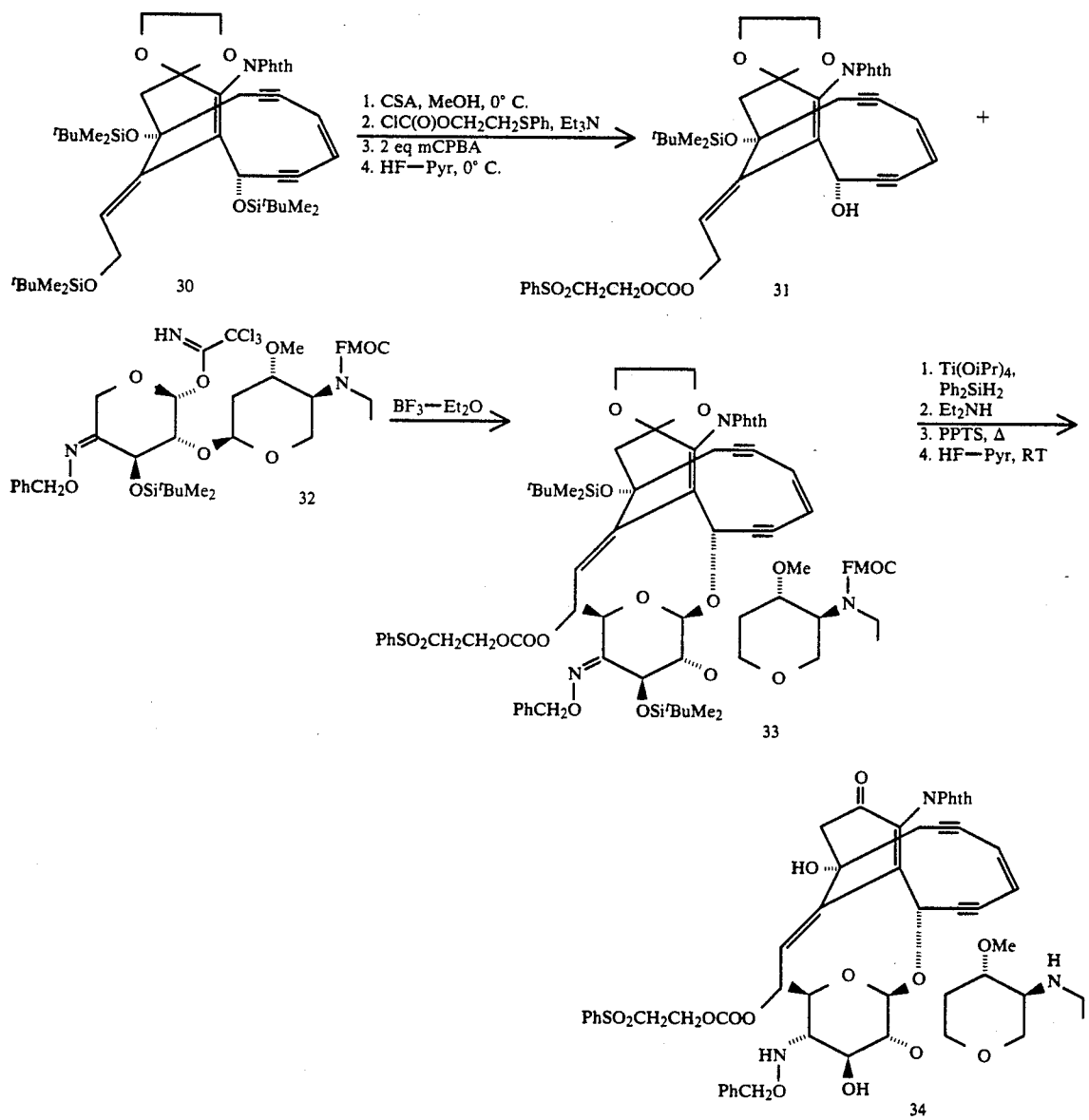

Starting with Scheme 9 in which NPhth is phthalimidoyl, Compound 30 is prepared from Compound 21 by reaction with $^tBuMe_2SiOTf$. Thereafter, reaction first with camphorsulfonic acid (CSA) in methanol at zero degrees C. provides the allylic primary alcohol. That alcohol is reacted 2-(thiophenoxy)ethoxycarbonyl chloride in the presence of triethylamine to provide the 2-(thiophenoxy)carbonate in step 2. Oxidation of the carbonate with two equivalents or a slight excess over two of a peroxide oxidant such as m-chloroperbenzoic acid (mCPBA) provides the phenylsulfonyl carbonate. The propargyl alcohol is deblocked with HF in pyridine at zero degrees C. to provide Compound 31.

Compound 31 is then reacted in boron trifluoride-etherate with the activated oligosaccharide Compound 32, a compound similar to Compound 53 but having a different silyl blocking group to form the protected chimer, Compound 33. Thereafter, reaction first with titanium tetra-isopropoxide and diphenylsilane reduces the oxime to the hydroxylamine; reaction with diethylamine removes the FMOC group; heating of the resulting compound with pyridinium p-toluenesulfonate removes the keto blocking group and treatment with HF in pyridine at room temperature removes the tertiary hydroxyl block group to provide a desired chimeric compound of Formula I, as Compound 34.

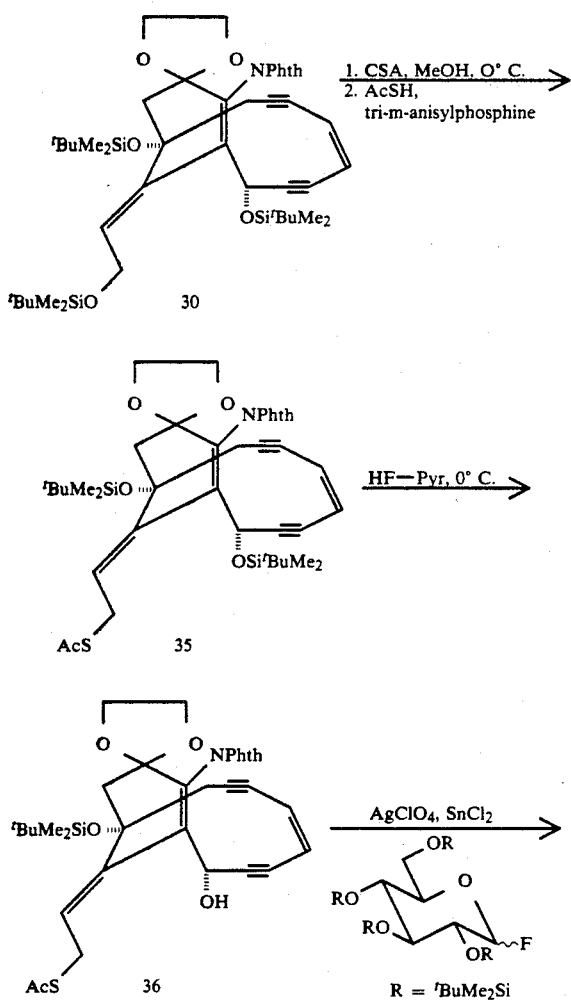

Scheme 10

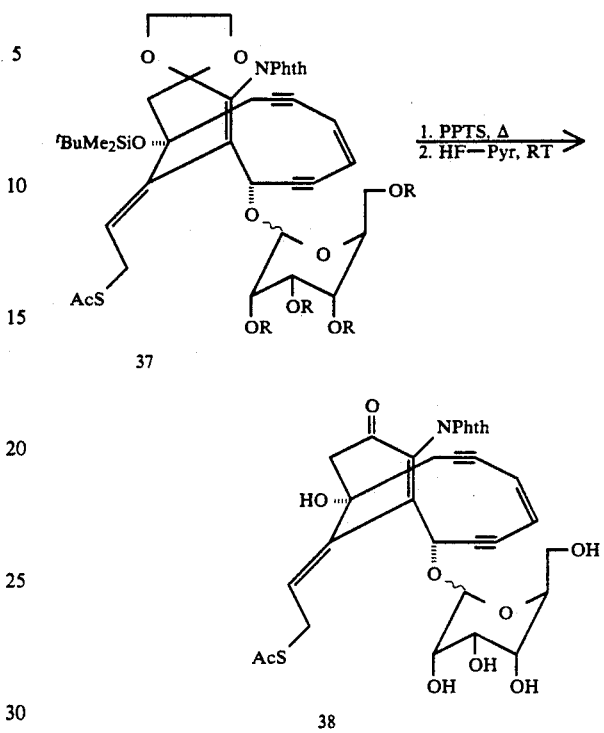

-continued
Scheme 10

Scheme 10 also begins with Compound 30, which is first reacted with CSA in methanol at zero degrees C to provide the allylic alcohol. Reaction of that alcohol with thioacetic acetic acid (AcSH) and tri-m-anisylphosphine as described in Haseltine et al., *J. Amer. Chem. Soc.*, 113:3850-3866 (1991) for preparation of Compound 109 therein provides the allylic thioacetate ester, Compound 35. Deblocking of the propargyl alcohol with HF in pyridine at zero degrees C provides Compound 36.

Compound 36 is then reacted with 1-fluoro-2,3,4,6-tetra(t-butyldimethylsilyl)glucose in the presence of silver perchlorate and stannous chloride to form the blocked chimer, Compound 37. Thereafter, reaction with PPTS and room temperature HF-pyridine removes the keto and tertiary hydroxyl groups, respectively, to provide the unblocked chimeric product, Compound 38.

II. Pharmaceutical Compositions

A compound of Formula I and particularly a chimeric compound or (—)-calicheamicinone is useful as a DNA cleaving agent, and also as an antimicrobial and a cytotoxic (antitumor) agent, as are dynemicin A, calicheamicin, esperamicin and neocarzinostatin. A chimeric compound of Formula I can also therefore be referred to as an "active agent" or "active ingredient".

DNA cleavage can be assayed using the techniques described hereinafter as well as those described by Mantlo et al., *J. Org. Chem.*, 54:2781 (1989); Nicolaou et al., *J. Am. Chem. Soc.*, 110:7147 (1989); Nicolaou et al., *J. Am. Chem. Soc.*, 110:7247 (1988) or Zein et al., *Science*, 240:1198 (1988) and the citations therein.

A compound of Formula I is useful against Gram-positive bacteria such as *S. aureus* and epidermis, *Micrococcus luteus* and *Bacillus subtillis* as is dynemicin A.

Such a compound also exhibits antimicrobial activity against *E. coli, Pseudomonas aeruginos, Candida albucans* and *Aspergillis fumigatus*. Activity of a compound of Formula I against the above microorganisms can be determined using various well known techniques. See, for example, Konishi et al., *J. Antibiotics, XLII:*1449 (1989). Antimicrobial and antitumor assays can also be carried out by techniques described in U.S. Pat. No. 4,837,206, whose disclosures are incorporated by reference, as well as by the procedures described hereinafter.

A before-described compound of Formula I can also be shown to undergo a Bergman cycloaromatization reaction in the presence of benzyl mercaptan, triethylamine and 1,4-cyclohexadiene as discussed in Haseltine et al., *J. Am. Chem. Soc.*, 111:7638 (1989). This reaction forms a tetracyclic reaction as is formed during DNA cleavage, and can be used as a co-screen to select more active compounds.

A pharmaceutical composition is thus contemplated that contains a before-described compound of Formula I, including (−)-calicheamicinone itself, as active agent dissolved or dispersed in a pharmaceutically acceptable carrier. A pharmaceutical composition is prepared by any of the methods well known in the art of pharmacy all of which involve bringing into association the active compound and the carrier therefor. For therapeutic use, a compound of Formula I can be administered in the form of conventional pharmaceutical compositions. Such compositions can be formulated so as to be suitable for oral or parenteral administration, or as suppositories. In these compositions, the agent is typically dissolved or dispersed in a physiologically tolerable carrier.

A carrier or diluent is a material useful for administering the active compound and must be "pharmaceutically acceptable" in the sense of being compatible with the other ingredients of the composition and not deleterious to the recipient thereof. As used herein, the phrases "physiologically tolerable" and "pharmaceutically acceptable" are used interchangeably and refer to molecular entities and compositions that do not produce an allergic or similar untoward reaction, such as gastric upset, dizziness and the like, when administered to a mammal. The physiologically tolerable carrier can take a wide variety of forms depending upon the preparation desired for administration and the intended route of administration.

As an example of a useful composition, a chimeric compound of the invention or (−)-calicheamicinone (active agent) can be utilized, dissolved or dispersed in a liquid composition such as a sterile suspension or solution, or as isotonic preparation containing suitable preservatives. Particularly well-suited for the present purposes are injectable media constituted by aqueous injectable buffered or unbuffered isotonic and sterile saline or glucose solutions, as well as water alone, or an aqueous ethanol solution. Additional liquid forms in which these compounds can be incorporated for administration include flavored emulsions with edible oils such as cottonseed oil, sesame oil, coconut oil, peanut oil, and the like, as well as elixirs and similar pharmaceutical vehicles. Exemplary further liquid diluents can be found in *Remmington's Pharmaceutical Sciences*, Mack Publishing Co., Easton, Pa. (1980).

An active agent can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain stabilizers, preservatives, excipients, and the like in addition to the agent. The preferred lipids are the phospholipids and the phosphatidyl cholines (lecithins), both natural and synthetic.

Methods of forming liposomes are known in the art. See, for example, Prescott, Et., *Methods in cell Biology*, Vol. XIV, Academic press, New York, N.Y. (1976), p.33 et seq.

An active agent can also be used in compositions such as tablets or pills, preferably containing a unit dose of the compound. To this end, the agent (active ingredient) is mixed with conventional tableting ingredients such as corn starch, lactose, sucrose, sorbitol, talc, stearic acid, magnesium stearate, dicalcium phosphate, gums, or similar materials as non-toxic, physiologically tolerable carriers. The tablets or pills can be laminated or otherwise compounded to provide unit dosage forms affording prolonged or delayed action.

It should be understood that in addition to the aforementioned carrier ingredients the pharmaceutical formulation described herein can include, as appropriate, one or more additional carrier ingredients such as diluents, buffers, flavoring agents, binders, surface active agents, thickeners, lubricants, preservatives (including antioxidants) and the like, and substances included for the purpose of rendering the formulation isotonic with the blood of the intended recipient.

The tablets or pills can also be provided with an enteric layer in the form of an envelope that serves to resist disintegration in the stomach and permits the active ingredient to pass intact into the duodenum or to be delayed in release. A variety of materials can be used for such enteric layers or coatings, including polymeric acids or mixtures of such acids with such materials as shellac, shellac and cetyl alcohol, cellulose acetate phthalate, and the like. A particularly suitable enteric coating comprises a styrene-maleic acid copolymer together with known materials that contribute to the enteric properties of the coating. Methods for producing enteric coated tablets are described in U.S. Pat. No. 4,079,125 to Sipos, which is herein incorporated by reference.

The term "unit dose", as used herein, refers to physically discrete units suitable as unitary dosages for administration to warm blooded animals, each such unit containing a predetermined quantity of the agent calculated to produce the desired therapeutic effect in association with the pharmaceutically acceptable diluent. Examples of suitable unit dosage forms in accord with this invention are tablets, capsules, pills, powder packets, granules, wafers, cachets, teaspoonfuls, dropperfuls, ampules, vials, segregated multiples of any of the foregoing, and the like.

An exemplary chimeric compound of the invention or (−)-calicheamicinone is present in such a pharmaceutical composition in an amount effective to achieve the desired result. For example, where in vitro DNA cleavage is the desired result, a compound of the invention can be utilized in an amount sufficient to provide a concentration of about 1.0 to about 5000 micromolar ($\mu$M) with a DNA concentration of about 0.02 $\mu$g/$\mu$L. As a cytotoxic (antitumor) agent, an effective amount of a compound of Formula I is about 0.1 to about 15 mg per kilogram of body weight or an amount sufficient to provide a concentration of about 0.01 to about 50 μg/mL to the bloodstream. A chimeric compound of the invention exhibits antimicrobial activity in a concentration range of about 0.01 ng to about 50 μg/mL. The above concentrations and dosages vary with the particular compound of the invention utilized as well as with the target, e.g., DNA, tumor, microbe, as is well known.

III. Methods

A compound of Formula I is useful in cleaving DNA, as a cytotoxic agent and also in inhibiting the growth of neoplastic cells, and is utilized in a method for effecting such a result. A compound of the invention is typically utilized in a before-described composition.

In accordance with such a method, DNA or target cells to be killed or whose growth is to be inhibited are contacted with a composition that contains an exemplary chimeric compound of the invention or (−)-calicheamicinone (active ingredient) present in an amount effective or sufficient for such a purpose, as discussed before, dissolved or dispersed in a physiologically tolerable (pharmaceutically acceptable) diluent. That contact is maintained for a time sufficient for the desired result to be obtained; i.e., DNA cleaved, cells killed or neoplastic cell growth inhibited.

Where the desired result is carried out in vitro, contact is maintained by simply admixing the DNA or target cells with composition and maintaining them together under the appropriate conditions of temperature and for cell growth to occur, as for control, untreated cells. Thus, a single admixing and contacting is typically sufficient for in vitro purposes. Exemplary studies using (−)-calicheamicinone to inhibit the in vitro growth of several cancer cell lines are discussed hereinafter.

The above method is also useful in vivo, as where a mammal such as a rodent like a rat, mouse, or rabbit, a farm animal like a horse, cow or goat, or a primate like a monkey, ape or human is treated. Here, contact of a composition and the cells to be killed or whose growth is to be inhibited is achieved by administration of the composition to the mammal by oral, nasal or anal administration or by introduction intravenously, subcutaneously or intraperitoneally. Thus, contact in vivo is achieved via the blood or lymph systems.

Although a single administration (admixture) and its resulting contact is usually sufficient to maintain the required contact and obtain a desired result in vitro, multiple administrations are typically utilized in vivo. Thus, because of a body's breakdown and excreting pathways, contact between an active ingredient of a composition and the target cells is typically maintained by repeated administration of a compound of the invention over a period of time such as days, weeks or months, or more, depending upon the target cells.

Experimental Section

General Techniques. NMR spectra were recorded on a Bruker AMX-500 instrument. IR spectra were recorded on Nicolet 205 or Perkin Elmer 1600 series FT-IR spectrophotometers. Optical rotations were recorded using a Perkin Elmer 241 polarimeter. High-resolution mass spectra (HRMS) were recorded on a VG ZAB-ZSE mass spectrometer under Fast Atom Bombardment (FAB) conditions.

All reactions were monitored by thin-layer chromatography carried out on 0.25 mm E. Merck silica gel plates (60F-254) using UV light, 7% ethanolic phosphomolybdic acid, or p-anisaldehyde solution and heat as developing agent. E. Merck silica gel (60, particle size 0.040–0.063 mm) was used for flash column chromatography.

All reactions were carried out under an argon atmosphere with dry, freshly distilled solvents under anhydrous conditions unless otherwise noted. Yields refer to chromatographically and spectroscopically ($^1$H NMR) homogeneous materials, unless otherwise stated.

EXAMPLE 1

1,4,7-Trioxaspiro[4.4]nonan-8-ol (Compound 7)

A solution of 1,4,7-trioxaspiro[4.4]nonan-8-one (prepared from tetronic acid and ethylene glycol) (3.81 g, 26.5 mmol) in dichloromethane (20 mL) at −78° C. was treated with 32 mL of 1.0 M DIBAL in dichloromethane (32.0 mmol). The mixture was stirred one hour, quenched at −78° C. with water (12 mL total) and stirred at 25° C. until complete decomposition of the aluminum complex (two hours). The granular precipitate of alumina was filtered off, and the product was purified by flash chromatography (ether) to give Compound 7 (3.32 g, 84 percent) as a low melting solid; $R_f$ =0.16 (Et$_2$O); IR (thin film) $\nu_{max}$ 3446 (bs), 1720 (w) cm$^{-1}$; $^1$H NMR (500 MHz, CDCl$_3$) δ 5.51 (bd, J =4.7 Hz, 1 H, OCHOH), 3.96-3.73 (m, 7 H, CH$_2$—O, OCH$_2$CH$_2$O, OH), 2.27 (dd, J =5.4, 13.7 Hz, 1 H, CHH), 2.05 (dd, J = 1.8, 13.7 Hz, 1 H, CHH); $^{13}$C NMR (125 MHz, CDCl$_3$) δ 114.8, 98.2, 72.5, 64.8, 64.7, 43.1; FAB HRMS (NBA/NaI) m/e 169.0477, M+NA$^+$ calcd for C$_6$H$_{10}$O$_4$ 169.0477.

EXAMPLE 2

2-(Hydroxymethyl)-2-[(2R, 3R)-2-hydroxy-3-[(2-methoxyethoxy)methoxy]pent-4-enyl]-1,3-dioxolane (Compound 10)

1-[(2-Methoxyethoxy) methoxy]-2-propene (4.40 g, 30.1 mmol) in THF (60 mL) was cooled to −78° C. sec-BuLi was added dropwise (22.0 mL of 1.3M solution in cyclohexane, 28.6 mmol) giving a canary-yellow solution. The reaction was stirred 10 minutes at −78° C., then (−)-B-methoxydiisopinocampheyl borane (9.04 g, 28.6 mmol) in THF (40 mL) was added dropwise (the yellow color discharged upon addition of the last few drops to give a colorless solution). The reaction was stirred one hour at −78° C., BF$_3$.OEt$_2$ was added (4.18 mL, 34.3 mmol), and the reaction mixture was cooled down to −96° C. The hemiacetal Compound 7 (3.79 g, 26.0 mmol) in THF (25 mL) was then slowly added dropwise. The colorless solution was maintained at −96° C. for three hours, then allowed to slowly warm to 25° C. over several hours. The solvent was removed in vacuo, and the residue dissolved in ether (100 mL). The solution was treated with 30 percent hydrogen peroxide (20 mL) and 4 pellets NaOH (NB exothermic). The reaction mixture was stirred overnight, separated, and the aqueous layer extracted with dichloromethane (3×50 mL), the organic extracts were concentrated, and the residue purified by flash chromatography (ether → EtOAc → 4 percent methanol/EtOAc) to give Compound 10 (6.64 g, 87 percent) as a colorless oil; $R_f$ =0.28 (4 percent MeOH in EtOAc); $[a]_D^{25}$ = −60.2° (c 3.6, CH$_2$Cl$_2$); IR (thin film) $\nu_{max}$ 3420, 1640 cm$^{-1}$; $^1$H NMR (500 MHz, CDCl$_3$) δ 5.63 (m, 1 H, CH=CH$_2$), 5.25-5.21 (m, 2 H, CH=CH$_2$), 4.65

(ABq, J =6.9 Hz, Δν =36 Hz, 2 H, OCH2O), 3.93–3.86 (m, 7 H, CH—OH, ethylene ketal, CH—OMEM, O—CHH—CH2OMe), 3.79 (m, 1 H, OCHH—CH2OMe), 3.74 (m, 1 H, O—CH2—CHH—OMe), 3.56 (m, 1 H, O—CH2—CHH—OMe), 3.51–3.43 (m, 4 H, CH2OH, OH), 3.29 (s, 3 H, OMe), 1.80 (m, 2 H, CH2); $^{13}$C NMR (125 MHz, CDCl3) δ 134.2, 119.9, 109.8, 93.8, 80.7, 71.5, 69.4, 67.1, 65.0, 65.0, 64.8, 58.8, 37.4; FAB HRMS (NBA/CsI) m/e 425.0590, M+Cs+ calcd for C13H24O7 425.0576.

EXAMPLE 3

(3aS,4R,5R)-5-Benzoyloxy-3,3a,4,5,6,7-hexahydro-4-[(2-methoxyethoxy)methoxy]spiro[2,1-benzisoxazole-7,2'-[1,3]dioxolane] (Compound 12) and
(3aR,4R,5R)-5-Benzoyloxy-3,3a,4,5,6,7-hexahydro-4-[(2-methoxyethoxy)methoxy]spiro[2,1-benzisoxazole-7,2'-[1,3]dioxolane] (Compound 12a)

A.
2-[((tert-Butyldimethylsilyl)oxy)methyl]-2-[(2R,3R)-2-hydroxy-3-[(2-methoxyethoxy)methoxy]pent-4-enyl]-1,3-dioxolane (Compound 10-1)

A solution of Compound 10 (6.55 g, 22.4 mmol) in dichloromethane (40 mL) at zero degrees C was treated with imidazole (3.21 g, 47.2 mmol), and then TBSCl (3.47 g, 23.1 mmol) in dichloromethane (20 mL) and stirred for two hours. The mixture was poured into saturated aqueous sodium bicarbonate solution (100 mL), extracted with dichloromethane (3×50 mL), concentrated, and the residue purified by flash chromatography (ether) to give Compound 10-1 (8.88 g, 98 percent) as a colorless oil; $R_f$ =0.51 (Et2O); $[α]_D^{25}$ = −33.3° (c 5.3, CH2Cl2); IR (thin film) $ν_{max}$ 3490 cm$^{-1}$; $^1$H NMR (500 MHz, CDCl3) δ 5.77 (m, 1 H, CH=CH2), 5.30–5.26 (m, 2 H, CH=CH2), 4.73 (ABq, J =6.5 Hz, Dn =40 Hz, 2 H, OCH2O), 4.03–3.95 (m, 5 H, CH—OH, ethylene ketal), 3.93 (dd, J =5.4, 10.0 Hz, 1 H, CH—OMEM), 3.82 (m, 1 H, OCHH—CH2—OMe), 3.61 (m, 1 H, OCHH—CH2—OMe), 3.55 (ABq, J =10.4 Hz, Dn =23 Hz, 2 H, CH2—OTBS), 3.53 (m, 2 H, OCH2CH2-13 OMe), 3.48 (bs, 1 H, OH), 3.37 (s, 3 H, OMe), 1.94 (dd, J =1.4, 14.9 Hz, 1 H, CHH), 1.83 (dd, J =10.0, 14.9 Hz, 1 H, CHH), 0.88 (s, 9 H, $^t$Bu), 0.04 (s, 6 H, SiMe2); $^{13}$C NMR (125 MHz, CDCl3) δ 134.7, 119.3, 110.4, 92.9, 80.2, 71.7, 69.5, 67.0, 66.2, 65.5, 65.1, 65.1, 58.9, 37.2, 25.8, 18.2, −5.5; FAB HRMS (NBA/CsI) m/e 539.1430, M+Cs+ calcd for C19H38O7Si 539.1441.

B.
2-[(2R,3R)-2-Benzoyloxy-3-[(2-methoxyethoxy)methoxy]pent-4-enyl]-2-[(tert-butyldimethylsilyl)oxy]methyl-1,3-dioxolane (Compound 10-2)

Silyl ether Compound 10-1 (6.02 g, 14.8 mmol) was dissolved in dichloromethane (10 mL) and pyridine (4.8 mL, 59.2 mmol), benzoyl chloride (3.44 mL, 29.6 mmol) plus a spatula tip of DMAP were added. The solution was stirred at 25° C. for 12 hours, diluted with dichloromethane (200 mL) and washed with saturated copper sulphate solution (2×100 mL). The aqueous layers were extracted with further dichloromethane (3×100 mL) and the combined organic layers were concentrated in vacuo to give a colorless oil. The product, Compound 10-2, was sufficiently pure for the next step. $R_f$ =0.06 (Et2O); $[α]_D^{25}$ = −26.7° (c 3.0, CH2Cl2); IR (thin film) $ν_{max}$ 1719 cm$^{-1}$; $^1$H NMR (500 MHz, CDCl3) δ 8.03 (d, J =8.2 Hz, 2 H, Bz), 7.50 (t, J =8.2 Hz, 1 H, Bz), 7.39 (t, J =8.2 Hz, 2 H, Bz), 5.72 (m, 1 H, CH=CH2), 5.52 (m, 1 H, CH—OBz), 5.32–5.27 (m, 2 H, CH=CH2), 4.69 (ABq, J =6.8 Hz, Dn =32 Hz, 2 H, O—CH2—O), 4.22 (t, J =6.8 Hz, 1 H, CH—OMEM), 3.98–3.82 (m, 4 H, ethylene ketal), 3.71–3.36 (m, 4 H, O—CH2CH2-O), OMe), 3.48 (ABq, J =10.2 Hz, Dn =39 Hz, 2 H, CH2—OTBS), 3.32 (s, 3 H, OMe), 2.17–2.08 (m, 2 H, CH2), 0.84 (s, 9 H, $^t$Bu), 0.00 (2s, 6 H, SiMe2); $^{13}$C NMR (125 MHz, CDCl3) δ 165.9, 133.9, 132.7, 130.6, 129.6, 128.2, 120.0, 109.6, 92.8, 78.3, 71.6, 70.7, 66.9, 66.2, 65.4, 65.3, 58.9, 34.4, 25.8, 18.2, −5.5; FAB HRMS (NBA/CsI) m/e 643.1703, M+Cs+ calcd for C26H42O8Si 643.1703.

C.
2-[(2R,3R)-2-Benzoyloxy-3-[(2-methoxyethoxy)methoxy]pent-4-enyl]-2-hydroxymethyl-1,3-dioxolane (Compound 10-3)

The crude Compound 10-2 (14.8 mmol) was dissolved in THF (300 mL), 90 mL of 1.0 M TBAF in THF was added, and the reaction mixture was heated at 50° C. for three hours. The solution was concentrated in vacuo and the residue was purified by flash chromatography (ether → EtOAc) to give Compound 10-3 (5.86 g, 100 percent over two steps) as a colorless oil. $R_f$ =0.20 (Et2O); $[α]_D^{25}$ = −30.0° (c 0.55, CH2Cl2); IR (thin film) $ν_{max}$ 3465, 1715 cm$^{-1}$; $^1$H NMR (500 MHz, CDCl3) δ 8.03 (d, J =7.2 Hz, 2 H, Bz), 7.53 (t, J =7.2 Hz, 1 H, Bz), 7.41 (t, J =7.2 Hz, 2 H, Bz), 5.73 (ddd, J =6.8, 10.8, 17.2 Hz, 1 H, CH=CH2), 5.51 (ddd, J =5.0, 6.4, 10.3 Hz, 1 H, CH—OBz), 5.34–5.29 (m, 2 H, CH=CH2), 4.71 (ABq, J =8.1 Hz, Dn =30 Hz, 2 H, O—CH2—O), 4.26 (dd, J =5.0, 6.8 Hz, 1 H, CH—OMEM), 4.03–3.88 (m, 4 H, ethylene ketal), 3.74 (m, 1 H, OCHH—CH2—OMe), 3.56–3.41 (m, 6 H, O—CHH—CH2—OMe, CH2—OH); $^{13}$C NMR (125 MHz, CDCl3) δ 165.9, 133.8, 132.9, 130.2, 129.7, 128.2, 120.0, 109.2, 93.0, 78.0, 71.6, 70.8, 67.0, 65.2, 65.2, 65.1, 58.9, 34,4; FAB HRMS (NBA/CsI) m/e 529.0861, M+Cs+ calcd for C20H28O8 529.0839.

D.
(E)-2-[(2R,3R)-2-Benzoyloxy-3-[(2-methoxyethoxy)methoxy] pent-4-enyl]-1,3-dioxolan-2-carboxaldehyde, oxime (Compound 10-4)

Oxalyl chloride (2.55 mL, 29.0 mmol) in 20 mL dichloromethane at −78° C. was treated dropwise with DMSO (2.84 mL, 40 mmol) in 10 mL dichloromethane. The mixture was stirred 30 minutes at −78° C., and then alcohol Compound 10-3 (5.86 g, 14.8 mmol) in dichloromethane (40 mL) was added dropwise. The reaction mixture was stirred 30 minutes at −78° C., and then triethylamine was added (20 mL, 145 mmol). The reaction mixture was stirred 30 minutes at −78° C., and then allowed to warm slowly to 25° C. over 30 minutes. The reaction mixture was poured into sodium bicarbonate solution (100 mL), extracted with dichloromethane (3×100 mL), and the extracts concentrated. The residue was dissolved in ethanol (60 mL) and hydroxylamine hydrochloride (3.14 g, 3 equivalents) dissolved in 30 mL water were added. The solution was stirred for 15 minutes, poured into brine (200 mL) and extracted with dichloromethane (3×200 mL). The organic extracts were concentrated and the residue purified by flash chromatography (ether) to give oxime Compound 10-4 (5.33 g, 88 percent over two steps) as a colorless oil; $R_f$ =0.29 (70 percent Et$_2$O in petroleum ether); [a]$_D^{25}$ =−32.0° (c 0.44, CH$_2$Cl$_2$); IR (thin film) $\nu_{max}$ 3380, 1718 cm$^{-1}$; $^1$H NMR (500 MHz, CDCl$_3$) δ 8.03 (d, J =7.1 Hz, 2 H, Bz), 7.99 (bs, 1 H, =N—OH), 7.52 (t, J =7.1 Hz, 2 H, Bz), 7.41 (t, J =7.1 Hz, 2 H, Bz), 7.29 (s, 1 H, CH=N), 5.73 (ddd, J =6.8, 10.4, 17.1 Hz, 1 H, CH=CH$_2$), 5.60 (m, 1 H, CH—OBz), 5.34-5.29 (m, 2 H, CH=CH$_2$), 4.71 (ABq, J =6.8 Hz, Dn =29 Hz, 2 H, O—CH$_2$—O), 4.27 (dd, J =5.1, 6.8 Hz, 1 H, CH—O-MEM), 4.06-3.83 (m, 4 H, ethylene ketal), 3.76 (m, 1 H, O—CHH—CH$_2$—OME), 3.57-3.42 (m, 3 H, OCHH—CH$_2$—OMe), 3.35 (s, 3 H, OMe), 2.32-2.30 (m, 2 H, CH$_2$); $^{13}$C NMR (125 MHz, CDCl$_3$) δ 165.8, 149.2, 133.6, 132.8, 130.3, 129.7, 128.2, 120.1, 105.8, 92.9, 77.8, 71.6, 70.0, 67.0, 65.1, 65.1, 58.9, 36.1; FAB HRMS (NBA/CsI) m/e 542.0776, M+Cs$^+$ calcd for C$_{20}$H$_{27}$NO$_8$ 542.0791.

E. Compounds 12a and 12b

A solution of oxime Compound 10-4 (19.7 g, 48.2 mL) in dichloromethane (1 L) was treated at zero degrees C with sodium hypochlorite (160 mL) of a 5 percent aqueous solution) and vigorously stirred for two hours. The reaction mixture was separated and the aqueous layer extracted with dichloromethane (3×150 mL), the organic extracts were dried (Na$_2$SO$_4$), concentrated, and purified by flash chromatography (70 percent ether in petroleum ether) to give Compound 12 (10.0 g, 51 percent) followed by Compound 12a in which the bridgehead hydrogen is trans to the OMEM group. (2.71 g., 14 percent). A 20 percent yield of an open chain ester (Compound 12-b) was also obtained.

Data for Compound 12. Solid, m.p. =97°-98° C. (from Et$_2$O); R$_f$=0.38 (Et$_2$O); [a]$_D^{25}$ = −20.4° (c 2.1, CH$_2$Cl$_2$); IR (thin film) $\nu_{max}$ 1726 cm$^{-1}$; $^1$H NMR (500 MHz, CDCl$_3$) δ 8.00 (d, J =8.6 Hz, 2 H, Bz), 7.57 (t, J =8.6 Hz, 1 H, Bz), 7.43 (t, J =8.6 Hz, 2 H, Bz), 5.47 (ddd, J =4.6, 9.2, 12.0 Hz, 2 H, O—CH$_2$—O), 4.68 (dd, J =8.3, 10.8 Hz, 1 H, CHH—O—N), 4.33 (dd, J =8.3, 9.8 Hz, 1 H, CHH—O—N), 4.21 (m, 1 H, ethylene ketal), 4.12 (m, 1 H, ethylene ketal), 4.04 (m, 1 H, ethylene ketal), 3.93 (m, 1 H, ethylene ketal), 3.84 (t, J =9.2 Hz, 1 H, CH—OMEM), 3.69 (ddd, J =4.6, 9.8, 10.8 Hz, 1 H, CH—C=N), 3.67-3.46 (m, 4 H, O—CH$_2$—CH$_2$—OMe), 3.34 (s, 3 H, OMe), 2.43 (dd, J =4.6, 13.1 Hz, 1 H, CHH), 2.10 (dd, J =12.0, 13.1 Hz, CHH); $^{13}$C NMR (125 MHz, CDCl$_3$) δ 165.2, 155.1, 133.3, 129.7, 128.6, 128.2, 102.5, 95.9, 81.1, 74.1, 72.9, 71.4, 67.6, 65.9, 64.7, 59.1, 51.5, 39.1; FAB HRMS (NBA/CsI) m/e 540.0678, M+Cs$^+$ calcd for C$_{20}$H$_{25}$NO$_8$ 540.0635.

Data for Compound 12a. Oil; R$_f$=0.33 (Et$_2$O); [a]$_D^{25}$ = +34.7° (c 5.3, CH$_2$Cl$_2$); IR (thin film) $\nu_{max}$ 1720 cm$^{-1}$; $^1$H NMR (500 MHz, CDCl$_3$) δ 8.03 (d, J =7.8 Hz, 2 H, Bz), 7.54 (t, J =8.7 Hz, 1 H Bz), 7.42 (t, J =8.7 Hz, 2 H, Bz), 5.51 (q, J =3.2 Hz, 1 H, CH—OBz), 4.83 (ABq, J =7.1 Hz, Dn =57 Hz, 2 H, O—CH$_2$—)), 4.42 (dd, J =7.6, 11.8 Hz, 1 H, CH—O—N), 4.32 (t, J =7.6 Hz, 1 H, CH—O—N), 4.17 (m, 1 H, ethylene ketal), 4.05 (m, 1 H, ethylene ketal), 4.00 (m, 1 H, CH—OMEM), 3.98-3.90 (m, 3 H, CH—C=N, ethylene ketal), 3.76-3.68 (m, 2 H, O—CH$_2$CH$_2$—OMe), 3.54-3.50 (m, 2 H, O—CH$_2$CH$_2$—OMe), 3.34 (s, 3 H, OMe), 2.54 (dd, J =3.6, 15.2 Hz, 1 H, CHH), 3.29 (ddd, J =0.9, 2.6, 15.2 Hz, 1 H, CHH); $^{13}$C NMR (125 MHz, CDCl$_3$) δ 165.2, 154.8, 133.2, 129.9, 129.8, 128.3, 103.1, 96.0, 74.3, 71.5, 70.3, 68.8, 68.0, 65.1, 64.8, 59.0, 44.1, 35.7; FAB HRMS (NBA/CsI) m/e 540.0671, M+Cs$^+$ calcd for C$_{20}$H$_{25}$NO$_8$ 540.0635.

Data for Compound 12b. Oil; R$_f$=0.21 (Et$_2$O); [a]$_D^{25}$ = −36.0° (c 3.0, CH$_2$Cl$_2$); IR (thin film) $\nu_{max}$ 3480, 1736, 1725 cm$^{-1}$; $^1$H NMR (500 MHz, CDCl$_3$) δ 8.00 (d, J =7.9 Hz, 2 H, Bz), 7.53 (t, J =7.9 Hz, 1 H, Bz), 7.41 (t, J =7.9 Hz, 2 H, Bz), 5.73 (ddd, J =7.0, 10.0, 17.0 Hz, 1 H, CH=CH$_2$), 5.68 (ddd, J =3.9, 6.1, 9.0 Hz, 1 H, CH—OBz), 5.39-5.32 (m, 2 H, CH=CH$_2$), 4.71 (ABq, J =7.2 Hz, Dn =31 Hz, 2 H, O—CH$_2$—O), 4.36 (dd, J =5.9, 7.0 Hz, 1 H, CH—OMEM), 4.22-3.69 (m, 4 H, O—CH$_2$CH$_2$—OH), 3.68-3.41 (m, 4 H, O—CH$_2$CH$_2$—OMe), 3.33 (s, 3 H, OMe), 2.84 (dd, J =3.9, 16.1 Hz, 1 H, CHH), 2.75 (dd, J =9.0, 16.1 Hz, 1 H, CHH), 2.57 (bs, 1 H, OH); $^{13}$C NMR (125 MHz, CDCl$_3$) δ 170.2, 166.1, 133.3, 133.0, 129.7, 129.5, 128.4, 120.7, 93.0, 71.7, 71.6, 67.2, 66.5, 60.7, 60.7, 59.0, 36.0; FAB HRMS (NBA/CsI) m/e 515.0682, M+Cs$^+$ calcd for C$_{19}$H$_{26}$O$_8$ 515.0682.

EXAMPLE 4

(3aS,4R,5R)-3,3a,4,5,6,7-Hexahydro-4-[(2-methoxyethoxy)meth oxy]spiro[2,1-benzisoxazole-7,2'-[1,3]dioxolan]-5-one (Compound 13)

A.

(3aS,4R,5R)-5-Hydroxy-3,3a,4,5,6,7-hexahydro-4-[(2-methoxyethoxy) methoxy]spiro[2,1-benzisoxazole-7,2'-[1,3]dioxolane] (Compound 13a)

A solution of Compound 12 (10.0 g, 24.6 mmol) in anhydrous methanol (200 mL) at zero degrees C was treated with sodium methoxide (about 500 mg, catalytic) and stored at zero degrees C for 12 hours. The solution was poured into brine (200 mL) and extracted with dichloromethane (3×200 mL), the organic extracts were dried (Na$_2$SO$_4$), concentrated, and the residue purified by flash chromatography (ether) to give Compound 13a (7.44 g, 100 percent) as a white solid, m.p. =55°-56° C. (from Et$_2$O); R$_f$=0.13 (Et$_2$O); [a]$_D^{25}$ = −69° (c 1.1, CH$_2$Cl$_2$); IR (thin film) $\nu_{max}$ 3440 cm$^{-1}$; $^1$H NMR (500 MHz, CDCl$_3$) δ 4.81 (ABq, J =7.4 Hz, Dn =52 Hz, 2 H, O—CH$_2$—O), 4.58 (dd, J =8.5, 11.0 Hz, 1 H, CHH—O—N), 4.18 (dddd, J =2.4, 4.8, 6.8, 11.9 Hz, 1 H, CH—OH), 4.17 (t, J =8.5 Hz, 1 H, CHH—O—N), 4.12 (d, J =2.4 Hz, 1 H, OH), 4.05 (m, 2 H, ethylene ketal), 3.89 (ddd, J =7.3, 8.5, 11.0 Hz, 1 H, CH—C=N), 3.89 (dd, J =6.8, 7.3 Hz, 1 H, CH—O-MEM), 3.78 (m, 1 H, ethylene ketal), 3.69 (m, 1 H, ethylene ketal), 3.53 (m, 2 H, O—CH$_2$CH$_2$—OMe), 3.48 (m, 1 H, O—CHHCH$_2$—OMe), 3.36 (s, 3 H, OMe), 3.31 (m, 1 H, O—CHHCH$_2$—OMe), 2.27 (dd, J =4.8, 13.8 Hz, 1 H, CHH), 1.95 (dd, J =11.9, 13.8 Hz, 1 H, CHH); $^{13}$C NMR (125 MHz, CDCl$_3$) δ 155.8, 103.9, 96.4, 87.9, 73.8, 71.3, 70.0, 67.9, 65.7, 64.6, 59.0, 51.3, 40.9; FAB HRMS (NBA) m/e 304.1371, M+H$^+$ calcd for C$_{13}$H$_{21}$NO$_7$ 304.1396.

Compound 13. A solution of Compound 13a (7.67 g., 25.3 mmol) in acetone (200 mL) was cooled to zero degrees C and treated with Jones' reagent (19.0 mL of a 2.0M solution, 1.5 equivalents). The mixture was stored at zero degrees C for 12 hours, quenched with excess isopropyl alcohol, poured into brine (300 mL) and extracted with dichloromethane (3×300 mL). The organic extracts were dried (Na$_2$SO$_4$), concentrated, and rapidly filtered through a short plug of silica gel eluting with ether to give the ketone Compound 13 (7.24 g, 95 percent) as a white solid, m.p. =80°-82° C. (from Et$_2$O); R$_f$=0.28 (Et$_2$O); [a]$_D^{25}$ = +42.6° (c 0.44, CH$_2$Cl$_2$); IR (thin film) $\nu_{max}$ 1735 cm$^{-1}$; $^1$H NMR (500 MHz, CDCl$_3$) δ 4.81 (ABq, J =7.6 Hz, Dn =33 Hz, 2 H, O—CH$_2$—O), 4.68 (dd, 1 H, J =8.3, 10.6 Hz, 1 H, CHH—O—N), 4.40 (t, J =8.3 Hz, 1 H, CHH—O—N), 4.33 (d, J =11.4 Hz, 1 H, CH—OMEM), 4.23 (m, 1 H, ethylene ketal), 4.10 (m, 1 H, ethylene ketal), 3.93 (m, 1 H, ethylene ketal), 3.78 (ddd, J =8.3, 10.6, 11.4 Hz, 1 H, CH—C≡N), 3.65 (m, 2 H, O—CH$_2$CH$_2$—OMe), 3.52 (m, 2 H, O—CH$_2$CH$_2$—OMe), 3.38 (s, 3 H, OMe), 2.93 (ABq, J =14.4 Hz, Dn =112 Hz, 1 H, CH$_2$); $^{13}$C NMR (125 MHz, CDCl$_3$) δ 200.2, 154.8, 103.0, 94.8, 80.6, 74.1, 71.4, 67.8, 66.1, 65.0, 59.1, 50.9, 49.8; FAB HRMS (NBA) m/e 302.1251, M+H$^+$ calcd for C$_{13}$H$_{19}$NO$_7$ 302.1240.

EXAMPLE 5

(3aS,4R,5R)-5-Acetoxy-3,3a,4,5,6,7-hexahydro-4-[(2-methoxyethoxy)methoxy]-5-[2-(trimethylsilyl)ethynyl]-spiro[2,1-benzisoxa zole-7,2'-[1,3]dioxolane] (Compound 14)

A solution of (trimethylsilyl)acetylene (6.8 mL, 48.2 mmol) in THF (30 mL) was treated at zero degrees C with n-butyllithium (14.5 mL of a 2.5 M solution in hexanes, 36.2 mmol). To this solution was added dropwise a solution of Compound 13 (7.24 g, 24.1 mmol) in THF (150 mL) at −78° C. After 30 minutes at −78° C., acetic anhydride (11.4 mL, 120 mmol) was added, the cooling bath was removed, and the solution was stirred at 25° C. for three hours. The solution was poured into brine (200 mL), extracted with dichloromethane (3×300 mL), the organic extracts were dried (Na$_2$SO$_4$), concentrated, and the residue purified by flash chromatography (70 percent ether in petroleum ether) to give Compound 14 (8.30 g, 78 percent) as a white solid, m.p. =154.5°–155.0° C. (from Et$_2$O); R$_f$ =0.35 (70 percent Et$_2$O in petroleum ether); [a]$_D^{25}$ =+1.0° (c 1.4, CH$_2$Cl$_2$); IR (thin film) $\nu_{max}$ 1751 cm$^{-1}$; $^1$H NMR (500 MHz, CDCl$_3$) δ 4.97 (dd, J =8.1, 10.6 Hz, 1 H, CHH—O—N), 4.29 (dd, J =8.2, 10.6 Hz, 1 H, CHH—O—N), 4.11 (m, 1 H, ethylene ketal), 4.00 (m, 1 H, ethylene ketal), 3.93-3.85 (m, 3 H, ethylene ketal (2 H), O—CHHCH$_2$—OMe), 3.79 (ddd, J =8.1, 8.2, 10.1 Hz, 1 H, CH—C≡N), 3.72 (d, J =10.1 Hz, 1 H, CH—OMEM), 3.58-3.51 (m, 3 H, O—CHHCH$_2$—OMe), 3.37 (s, 3 H, OMe), 2.72 (ABq, J =15.5 Hz, Δν =615 Hz, CH$_2$), 2.06 (s, 3 H, OAc), 0.12 (s, 9 H, SiMe$_3$); $^{13}$C NMR (125 MHz, CDCl$_3$) δ 169.2, 154.9, 101.9, 101.0, 97.1, 92.0, 84.1, 75.0, 73.2, 71.3, 67.9, 65.1, 65.0, 59.1, 49.8, 40.8, 21.9, −0.4; FAB HRMS (NBA/CsI) m/e 574.0879, M+Cs$^+$ calcd for C$_{20}$H$_{31}$NO$_8$Si 574.0873.

EXAMPLE 6

(5R)-5-Acetoxy-4,5,6,7-tetrahydro-5-[2-(trimethylsilyl)ethynyl]spiro[2,1-benzisoxazole-7,2'-[1,3]dioxolan]-4-one (Compound 15)

A solution of Compound 14 (7.14 g, 16.2 mmol) in anhydrous dichloromethane (200 mL) was treated with zinc bromide (36.4 g, 162 mmol) and the mixture stirred at 25° C. for two hours. The mixture was poured into brine (200 mL), extracted with dichloromethane (3×200 mL), and the organic extracts were dried (Na$_2$SO$_4$), concentrated and the residue was rapidly filtered through a short plug of silica gel eluting with ether to give the sensitive crude alcohol ester, Compound 14a (5.91 g).

A solution of oxalyl chloride (5.7 mL, 65.5 mmol) in dichloromethane (40 mL) at −78° C. was treated with a solution of DMSO (9.3 mL, 131 mmol) in dichloromethane (40 mL) at −78° C. The solution was stirred for 30 minutes, and then the above crude alcohol Compound 14a in dichloromethane (40 mL) was added dropwise. The solution was stirred 30 minutes at −78° C., and then Et$_3$N (36.4 mL, 260 mmol) was added. The solution was stirred 30 minutes at −78° C. and then allowed to warm up to −20° C. The solution was poured into brine (200 mL) and extracted with dichloromethane (3×200 mL), the organic extracts were dried (Na$_2$SO$_4$), concentrated, and the residue purified by flash chromatography (30 percent ether in petroleum ether) to give isoxazole Compound 15 (3.07 g, 54 percent) as a white solid, m.p. =132°–133° C. decomp. (from Et$_2$O); R$_f$ =0.36 (30 percent Et$_2$O in petroleum ether); [a]$_D^{25}$ =+26.8° (C 2.3, CH$_2$Cl$_2$); IR (thin film) $\nu_{max}$ 1747, 1722, 1581 cm$^{-1}$; $^1$H NMR (500 MHz, CDCl$_3$) δ 9.03 (s, 1 H, C=CH—O), 4.36 (m, 1 H, ethylene ketal), 4.23 (m, 2 H, ethylene ketal), 4.11 (m, 1 H, ethylene ketal), 3.44 (d, J =13.8 Hz, 1 H, CHH), 2.63 (d, J =13.8 Hz, 1 H, CHH), 2.14 (s, 3 H, OAc), 0.14 (s, 9 H, SiMe$_3$); $^{13}$C NMR (125 MHz, CDCl$_3$) δ 181.7, 169.2, 162.0, 161.5, 115.6, 100.6, 97.8, 97.3, 77.1, 65.2, 64.9, 43.6, 21.1, −0.8; FAB HRMS (NBA) m/e 350.1065, M+H$^+$ calcd for C$_{16}$H$_{19}$NO$_6$Si 350.1060.

EXAMPLE 7

(E)-2-[(5R)-5-Acetoxy-4,5,6,7-tetrahydro-5-[2-(trimethylsilyl)ethynyl]spiro[spiro[2,1-benzisoxazole-7,2'-[1,3]dioxolan]-4-ylidene]acetic acid, methyl ester (Compound 16)

A solution of Compound 15 (3.02 g, 8.65 mmol) in toluene (80 mL) was treated with methyl (triphenylphosphoranylidene) acetate (14.5 g, 43.3 mmol) and stirred at 90° C. for 12 hours. The solution was concentrated and the residue was purified by flash chromatography (30 percent ether in petroleum ether) to give Compound 16 (2.94 g, 84 percent) as a colorless oil; R$_f$ =0.41 (30 percent Et$_2$O in petroleum ether); [a]$_D^{25}$ =+29.7° (c 2.7, CH$_2$Cl$_2$); IR (thin film) $\nu_{max}$ 1759, 1722, 1644, 1581 cm$^{-1}$; $^1$H NMR (500 MHz, CDCl$_3$) δ 9.57 (s, 1 H, C=CH—O), 6.86 (s, 1 H, C=CH—CO$_2$), 4.30 (m, 2 H, ethylene ketal), 4.15-4.07 (m, 2 H, ethylene ketal), 3.78 (s, 3 H, CO$_2$Me), 3.39 (d, J =13.9 Hz, 1 H, CHH), 2.53 (d, J =13.9 Hz), 1 H, CHH), 1.92 (s, 3 H, OAc), 0.21 (s, 9 H, SiMe$_3$); $^{13}$C NMR (125 MHz, CDCl$_e$) δ 168.7, 166.1, 161.6, 160.3, 138.4, 119.2, 111.4, 100.3, 99.6, 96.3, 76.0, 65.3, 64.8, 51.8, 44.1, 21.7, −0.4; FAB HRMS (NBA/CsI) m/e 538.0298, M+Cs$^+$ calcd for C$_{19}$H$_{23}$NO$_7$Si 538.0298.

EXAMPLE 8

(E)-2-[(5R)-5-Ethynyl-4,5,6,7-tetrahydro-5-hydroxyspiro[2,1-benzisoxazole-7,2'-[1,3]dioxolan]-4-ylidene]acetic acid, methyl ester (Compound 60)

A solution of Compound 16 (2.94 g, 7.26 mmol) in tetrahydrofuran-methanol (1:2, 40 mL) was treated with potassium carbonate (1 g, 1 equivalent) and stored at zero degrees C for two hours. The solution was poured into brine (100 mL) and extracted with dichloromethane (3×100 mL). The organic extracts were dried (Na$_2$SO$_4$), concentrated, and the residue purified by flash chromatography (ether) to give Compound 60 (2.05 g, 97 percent) as a white foam; R$_f$=0.32 (50 percent Et$_2$O in petroleum ether); [a]$_D^{25}$ =+14.8° (c 3.3, CH$_2$Cl$_2$); IR (thin film) $\nu_{max}$ 3444, 3285, 2117, 1717, 1642, 1582 cm$^{-1}$; $^1$H NMR (500 MHz, CDCl$_3$) δ 9,72 (s, 1 H, C=CH—O), 6.80 (s, 1 H, C=CH—CO$_2$), 4.43 (m, 1 H, ethylene ketal), 4.33 (m, 1 H, ethylene ketal), 4.24 (m, 1 H, ethylene ketal), 4.17 (m, 1 H, ethylene ketal), 3.78 (s, 3 H, CO$_2$Me), 3.68 (s, 1 H, OH), 2.79 (s, 1 H, C≡C—H), 2.73 (s, 2 H, CH$_2$); $^{13}$C NMR (125 MHz, CDCl$_3$) δ 166.4, 162.3, 159.6, 141.4, 117.0, 111.3, 100.4, 82.8, 76.2, 71.1, 65.3, 65.2, 51.8, 47.1; FAB HRMS (NBA/CsI) m/e 423.9797, M+Cs+ calcd for C$_{14}$H$_{13}$NO$_6$ 423,9797.

EXAMPLE 9

(E)-2-[(5R)-5-Ethynyl-4,5,6,7-tetrahydro-5-[(triethylsilyl)oxy]spiro[2,1-benzisoxazole-7,2′-[1,3]dioxolan]-4-ylidene]acetic acid, methyl ester (Compound 61)

A solution of Compound 60 (1.657 g, 5.69 mmol) in dichloromethane (10 mL) was treated with 2,6-lutidine (2.00 mL, 17.1 mmol) and triethylsilyl trifluoromethanesulfonate (2.58 mL, 11.4 mmol) at zero degrees C. The solution was stirred 30 minutes, anhydrous methanol (2 mL) was added, the mixture was poured into brine (50 mL) and extracted with dichloromethane (3×50 mL). The organic extracts were dried (Na$_2$SO$_4$), concentrated and purified by flash chromatography (20% Et$_2$O in petroleum ether) to give Compound 61 (2.204 g, 96 percent) as a white solid, m.p. =108 °–109° C. (from CH$_2$Cl$_2$); R$_f$=0.43 (30 percent Et$_2$O in petroleum ether); [a]$_D^{25}$ = −15.4° (c 2.8, CH$_2$Cl$_2$); IR (thin film) $\nu_{max}$ 3307, 2116, 1721, 1646 cm$^{-1}$; $^1$H NMR (500 MHz, CDCl$_3$) δ 9.50 (s, 1 H, C=CH—O), 6.57 (s, 1 H, C=CH—CO$_2$), 4.38–4.31 (m, 2 H, ethylene ketal), 4.18–4.10 (m, 2 H, ethylene ketal), 3.74 (s, 3 H, CO$_2$Me), 2.66 (s, 1 H, C}C—H), 2.61 (ABq, J =14.0 Hz, Δv =34 Hz, 2 H, CH$_2$), 0.92 (t, J =7.9 Hz, 9 H, Si(CH$_2$CH$_3$)$_3$), 0.70 (q, J =7.9 Hz, 6 H, Si(CH$_2$CH$_3$)$_3$); $^{13}$C NMR (125 MHz, CDCl$_3$) δ 166.5, 161.3, 160.7, 143.8, 114.5, 111.9, 100.6, 83.2, 76.9, 70.9, 65.0, 64.8, 51.6, 49.8, 6.8, 5.9; FAB HRMS (NBA/CsI) m/e 538.0652, M+Cs+ calcd for C$_{20}$H$_{27}$NO$_6$Si 538.0662.

EXAMPLE 10

(E)-2-[(5R)-4,5,6,7-Tetrahydro-5-[(triethylsilyl)oxy]-5-[(3Z)-6-trimethylsilyl-3-hexen-1,5-diynyl]spiro[2,1-benzisoxazole-7,2′-[1,3]dioxolan]-4-ylidene]acetic acid, methyl ester (Compound 62)

(Z)-(4-chloro-3-buten-1-ynyl)trimethylsilane (1.41 mL, 8.16 mmol) and n-butylamine (0.81 mL, 8.16 mmol) were added to a solution of Pd(Ph$_3$)$_4$ (628 mg, 0.54 mmol) in benzene (25 mL). The solution was stirred at 25° C. for 15 minutes and then added to a mixture of Compound 61 (2.204 g, 5.44 mmol) and CuI (207 mg, 1.09 mmol) in benzene (25 mL) at zero degrees C. The solution was stirred two hours at zero degrees C, poured into brine (100 mL) and extracted with dichloromethane (3×100 mL). The organic extracts were dried (Na$_2$SO$_4$), concentrated and purified by flash chromatography (10 percent Et$_2$O in petroleum ether) to give Compound 62 (2.606 g, 91 percent) as a colorless oil; R$_f$ =0.46 (30% Et20 in petroleum ether); [a]$_D^{25}$ = +17.4° (c .2.7, CH$_2$Cl$_2$); IR (thin film) $\nu_{max}$ 1720 cm$^{-1}$; $^1$H NMR (500 MHz, CDCl$_3$) δ 9.50 (s, 1 H, C=CH—O), 6.65 (s, 1 H, C=CH—CO$_2$), 5.86 (ABq, J =11.0 Hz, Dn =30 Hz, 2 H, CH=CH), 4.38–4.29 (m, 2 H, ethylene ketal), 4.15–4.09 (m, 2 H, ethylene ketal), 3.74 (s, 3 H, CO$_2$Me), 2.67 (ABq, J =14.1 Hz, Dn =61 Hz, 2 H, CH$_2$), 0.89 (t, J =7.3 Hz, 9 H, Si(CH$_2$CH$_3$)$_3$), 0.66 (m, 6 H, Si(CH$_2$CH$_3$)$_3$), 0.17 (s, 9 H, SiMe$_3$); $^{13}$C NMR (125 MHz, CDCl$_3$) δ 166.6, 161.2, 161.0, 143.7, 121.2, 118.6, 114.9, 112.0, 103.5, 101.3, 100.7, 95.5, 85.7, 72.1, 65.0, 64.6, 51.5, 50.0, 6.8, 5.9, −0.4; FAB HRMS (NBA/CsI) m/e 660.1213, M+Cs+ calcd for C$_{27}$H$_{37}$NO$_6$Si$_2$ 660.1214.

EXAMPLE 11

(E)-2-[(9R)-6-Amino-7-formyl-9-[(triethylsilyl)oxy]-9-[(3Z)-6-trimethylsilyl-3-hexen-1,5-diynyl]-1,4-dioxaspiro[4.5]dec-6-en]-8-ylidene]acetic acid, methyl ester (Compound 63)

A solution of Compound 62 (2.588 g, 4.91 mmol) in acetonitrile-water (50 mL, 5:1) was treated with molybdenum hexacarbonyl (1.30 g, 4.91 mmol) and heated to 80° C. for 90 minutes. Silica gel (20 g) was added and the mixture was evaporated to dryness. The powder was applied to the top of a flash column and eluted with 50 percent Et$_2$O in petroleum ether → Et$_2$O to give Compound 63 (2.077 g, 80 percent) as a colorless oil; R$_f$ =0.41 (Et$_2$O); [a]$_D^{25}$ = +4.9° (c 2.8, CH$_2$Cl$_2$); IR (thin film) $\nu_{max}$ 3381, 3280, 3195, 1704, 1643, 1597 cm$^{-1}$; $^1$H NMR (500 MHz, CDCl$_3$) δ 9.22 (s, 1 H, CHO), 6.25 (s, 1 H, C=CH—CO$_2$), 5.84 (ABq, J =10.9 Hz, Dn =30 Hz, 2 H, CH=CH ), 4.09–4.02 (m, 4 H, ethylene ketal), 3.68 (s, 3 H, CO$_2$Me), 2.45 (ABq, J =14.2 Hz, Δv =42 Hz, 2 H, CH$_2$), 0.93 (t, J =8.0 Hz, 9 H, Si(CH$_2$CH$_3$)$_3$], 0.68 (q, J =8.0 Hz, 6 H, Si(CH$_2$CH$_3$)$_3$), 0.19 (s, 9 H, SiMe$_3$); $^{13}$C NMR (125 MHz, CDCl$_3$) δ 190.0, 167.7, 158.3, 153.1, 120.8, 118.9, 109.8, 103.2, 103.2, 102.2, 101.5, 97.8, 83.7, 70.6, 65.5, 65.4, 51.2, 49.7, 7.0, 5.9, −0.3; FAB HRMS (NBA/CsI) m/e 662.1370, M+Cs+ calcd for C$_{27}$H$_{39}$NO$_6$Si$_2$ 662.1370.

EXAMPLE 12

(E)-2-[(9R)-6-Amino-7-formyl-9-[(3Z)-3-hexen-1,5-diynyl]-9-[(triethylsilyl)oxy]-1,4-dioxaspiro[4.5]dec-6-en]-8-ylidene]acetic acid, methyl ester (Compound 64)

A solution of Compound 75 (1.962 g, 3.71 mmol) in tetrahydrofuran-methanol (50 mL, 1:2) was treated with K$_2$CO$_3$ (513 mg, 1 equivalent) and stirred at zero degrees C for two hours. The solution was poured into brine (100 mL), extracted with dichloromethane (3×100 mL), the organic extracts were dried (Na$_2$SO$_4$), concentrated and purified by flash chromatography (ether) to give Compound 64 (1.567 g, 92 percent) as a white solid, m.p. =109°–110° C. (from Et$_2$O); R$_f$ =0.33 (Et$_2$O); [a]$_D^{25}$ = −29.9° (c 2.5, CDCl$_3$); IR (thin film) $\nu_{max}$ 3404, 3281, 3195, 1707, 1647, 1604 cm$^{-1}$; $^1$H NMR (500 MHz, CDCl$_3$) δ 9.55 (bs, 1 H, NH), 9.20 (s, 1 H, CHO), 6.29 (s, 1 H, C=CH—CO$_2$), 5.88 (d, J =10.4 Hz, 1 H, CH=CH), 5.85 (bs, 1 H, NH), 5.81 (dd, J =2.4, 10.4 Hz, 1 H, CH=CH), 4.09–4.01 (m, 4 H, ethylene ketal), 3.68 (s, 3 H, CO$_2$Me), 3.33 (d J =2.4 Hz, 1 H, C≡C—H), 2.42 (ABq, J =13.9 Hz, Δv =74 Hz, 2 H, CH$_2$), 0.93 (t, J =7.6 Hz, 9 H, Si(CH$_2$CH$_3$)$_3$), 0.69 (q, J =7.6 Hz, 6 H, Si(CH$_2$CH$_3$)$_3$); $^{13}$C NMR (125 MHz, CDCl$_3$) δ 190.1, 167.9, 158.1, 153.0, 120.5, 119.8, 109.8, 103.2, 102.5, 98.0, 85.4, 83.2, 80.4, 70.5, 65.5, 65.4, 51.2, 49.5, 6.9, 5.8; FAB HRMS (NBA/CsI) m/e 590.0975, M+Cs+ calcd for C$_{24}$H$_{31}$NO$_6$Si 590.0975.

EXAMPLE 13

(E)-2-[(9R)-7-Formyl-9-[(3Z)-3-hexen-1,5-diynyl]-6-N-phthal imido-9-[(triethylsilyl)oxy]-1,4-dioxaspiro[4.5]dec-6-en]-8-ylidene] acetic acid, methyl ester (Compound 66)

A solution of Compound 64 (1.543 g, 3.38 mmol) in nitromethane (130 mL) at zero degrees C was treated with pyridine (109 mL, 13.5 mmol) followed by the dropwise addition of phthaloyl chloride (0.68 mL, 4.73 mmol) in nitromethane (10 mL) over 15 minutes. The solution was stirred at zero degrees C for 30 minutes, poured into brine (200 mL) and extracted with dichloromethane (3×200 mL). The extracts were dried (Na$_2$SO$_4$), concentrated, azeotroped with toluene, and dissolved in dichloromethane (100 mL). Silica gel (about 20 g) was added and the mixture stirred at 20° C. for two hours. The slurry was then concentrated to dryness and washed with 15 percent MeOH in EtOAc. The filtrate was dissolved in nitromethane (30 mL) and treated with Ac$_2$O (2.84 mL, 30 mmol). After stirring for one hour at 25° C., the solution was concentrated, azeotroped with toluene (three times), and the residue was dissolved in dichloromethane (100 mL). Silica gel (about 20 g) was added and the slurry stirred for two hours at 25° C., concentrated to dryness, and the resulting powder was applied to the top of a flash column and eluted with 20 percent Et$_2$O in petroleum ether → 50 percent Et$_2$O in petroleum ether → 10 percent MeOH in EtOAc to give Compound 66 (1.27 g) followed by the phthalamic acid (430 mg).

The phthalamic acid was azeotroped with benzene, dissolved in nitromethane (5 mL), and acetic anhydride (1 mL) was added. The solution was stirred one hour at 25° C. and worked up as above to give a further 280 mg of Compound 66 followed by the phthalamic acid (80 mg). Combined yield of Compound 66 =1.55 g (78 percent).

Data for Compound 66. White foam; R$_f$ =0.38 (70 percent Et$_2$O in petroleum ether); [a]$_D^{25}$ = +2.9° (c 3.2 CDCl$_3$); IR (thin film) $v_{max}$ 32.96, 3274, 1733, 1716 cm$^{-1}$; $^1$H NMR (500 MHz, CDCl$_3$) δ 9.38 (s, 1 H, CHO), 7.92–7.87 (m, 2 H, phth), 7.75 (m, 2 H, phth), 6.63 (s, 1 H, C=CH—CO$_2$), 6.07 (d, J =11.1 Hz, 1 H, CH=CH), 5.87 (dd, J =2.3, 11.1 Hz, 1 H, CH=CH), 3.94–3.89 (m, 2 H, ethylene ketal), 3.84–3.75 (m, 2 H, ethylene ketal), 3.68 (s, 3 H, CO$_2$Me), 3.31 (d, J =2.3 Hz, 1 H, C$_{57\,C-H}$), 2.54 (ABq, J =13.5 Hz, Δv =52 Hz, 2 H, CH$_2$), 0.98 (t, J =7.6 Hz, 9 H, Si(CH$_2$CH$_3$)$_3$), 0.78 (m, 6 H, Si(CH$_2$CH$_3$)$_3$); $^{13}$C NMR (125 MHz, CDCl$_3$) δ 185.3, 166.4, 166.3, 166.2, 148.0, 137.5, 136.8, 134.3, 134.3, 132.0, 132.0, 124.0, 123.9, 120.6, 119.6, 117.8, 105.3, 95.4, 85.3, 85.2, 80.7, 71.0, 71.0, 65.7, 65.7, 7.0, 5.9; FAB HRMS (NBA/CsI) m/e 720.1060, M+Cs$^+$ calcd for C$_{32}$H$_{33}$NO$_8$Si 720.1030.

EXAMPLE 4

(E)-2-[(1R,8R)-8-Hydroxy-10-N-phthalimido-1-[(triethylsilyl) oxy]spiro[bicyclo[7.3.1]trideca-4,9-diene-2,6-diyne-11,2'-1,3]dioxo lan]-13-ylidene]acetic acid, methyl ester (Compound 67)

A solution of Compound 66 (1.55 g, 2.64 mmol) in toluene (350 mL) was cooled in a methanol-dry ice-liquid nitrogen bath to just above the freezing point of the reaction mixture (about −90° C.) and KHMDS (2.90 mL of a freshly prepared 1.0M solution in THF, 2.90 mmol) was added dropwise. The solution was stirred five minutes, and then quenched at −90° C. with acetic acid (8.7 mL of a 1.0M solution in toluene). The mixture was poured into brine (300 mL), extracted, and the aqueous layer extracted with dichloromethane (3×200 mL). The organic extracts were dried (Na$_2$SO$_4$), concentrated, and purified by flash chromatography (50 percent→70 percent ether in petroleum ether) to give an inseparable 9:1 mixture of Compounds 67 and 69 (686 mg, 44 percent) as a white solid, m.p. >200° C. decomp. (from CH$_2$Cl$_2$); R$_f$=0.32 (70 percent Et$_2$O inpetroleum ether); [a]$_D^{25}$ = −235° (c 2.4, CH$_2$Cl$_2$); IR (thin film) $v_{max}$ 3495, 1721 cm$^{-1}$; $^1$H NMR (500 MHz, CDCl$_3$) δ 7.88–7.85 (m, 2 H, phth), 7.70–7.68 (m, 2 H, phth), 6.26 (s, 1 H, C=CH—CO$_2$), 6.00 (dd, J =1.1, 9.6 Hz, 1 H, CH=CH), 5.88 (dd, J =0.8, 9.6 Hz, 1 H, CH=CH), 5.39 (bs, 1 H, CH—CH), 3.87–3.69 (m, 4 H, ethylene ketal), 3.77 (s, 3 H, CO$_2$Me), 3.21 (bs, 1 H, OH), 2.58 (ABq, J =13.5 Hz, Δv =300 Hz, 2 H, CH$_2$), 0.99 [t, J =7.4 Hz, 9 H, Si(CH$_2$CH$_3$)$_3$], 0.79–0.72 (m, 6 H, Si(CH$_2$CH$_3$)$_3$); $^{13}$C NMR (125 MHz, CDCl$_3$) δ 168.3, 167.1, 166.0, 156.2, 148.8, 133.9, 133.7, 132.3, 132.2, 131.1, 123.7, 123.7, 122.9, 122.7, 113.6, 105.3, 98.9, 98.5, 91.2, 86.3, 71.3, 66.0, 65.2, 64.9, 52.8, 52.1, 7.1, 5.9; FAB HRMS (NBA/CsI) m/e 720.1032, M+Cs$^+$ calcd for C$_{32}$H$_{33}$NO$_8$Si 720.1030.

EXAMPLE 15

(1'S,5'R)-5',6'-Dihydro-8'-N-phthalimido-5'-triethylsilyl)oxy spiro[1,3-dioxolane-2,7'(3'H)-[1,5][3]hexene[1,5-]diyno[1H-2]benzo pyran]-3'-one (Compound 69)

A solution of Compound 69 (686 mg, 1.17 mmol) in CH$_2$Cl$_2$ (15 mL) was treated with pyridine (1.90 mL, 26 mmol), methanesulfonyl chloride (0.89 mL, 11.5 mmol) and DMAP (20 mg, catalytic) at zero degrees C. The solution was stirred at zero degrees C for two hours, poured into brine (50 mL) and extracted with CH$_2$Cl$_2$ (3×50 mL). The combined organic extracts were dried (Na$_2$SO$_4$), concentrated, and purified by flash chromatography eluting with ether to give mesylate Compound 68 as a white solid.

The mesylate Compound 68 was dissolved in benzene (100 mL), and pyridine (0.19 mL, 2.6 mmol) followed by silica gel (4 g) were added. The suspension was stirred five hours at 25° C., concentrated to give a powder, and applied to the top of a flash chromatography column and eluted with ether to give pure lactone Compound 69 (585 mg, 90 percent) as a white foam; R$_f$ =0.43 (20 percent EtOAc in PhH); [a]$_D^{25}$ = −406° (c 0.82, CH$_2$Cl$_2$); IR (thin film) $v_{max}$ 1730 cm$^{-1}$; $^1$H NMR (500 MHz, CDCl$_3$) δ 7.96–7.90 (m, 2 H, phth), 7.80–7.78 (m, 2 H, phth), 6.26 (s, 1 H, C=CH—CO$_2$), 6.06 (d, J =9.7 Hz, 1 H, CH=CH), 5.90 (dd, J =1.6, 9.7 Hz, 1 H, CH=CH), 5.73 (d, J =1.6 Hz, 1 H, C=C—CH—O), 3.96–3.86 (m, 3 H, ethylene ketal), 3.58–3.54 (m, 1 H, ethylene ketal), 2.51 (ABq, J =13.2 Hz, Δv =24 Hz, 2 H, CH$_2$), 1.01 (t, J =8.5 Hz, 9 H, Si(CH$_2$CH$_3$)$_3$), 0.85–0.70 (m, 6 H, Si(CH$_2$CH$_3$)$_3$); $^{13}$C NMR (125 MHz, CDCl$_3$) δ 166.4, 165.7, 161.7, 153.1, 134.7, 134.6, 131.7, 131.6, 125.8, 125.4, 124.2, 124.1, 123.1, 111.7, 105.7, 98.8, 94.9, 91.6, 90.8, 69.5, 68.0, 65.6, 65.4, 46.4, 6.9, 5.9; FAB HRMS (NBA/CsI) m/e 688.0768, M+Cs$^+$ calcd for C$_{31}$H$_{29}$NO$_7$Si 688.0768.

EXAMPLE 16

(1'S,5'R)-8'-Amino-5',6'-dihydro-5'-(triethylsilyl)oxyspiro[1,3-dioxolane-2,7'(3'H)-[1,5][3]hexene[1,5-]diyno[1H-2]benzopyran]-3'-one (Compound 70)

A solution of Compound 69 (585 mg, 1.054 mmol) in benzene (50 mL) was treated with methylhydrazine (0.70 mL, 13 mmol) and stirred for 30 minutes at 25° C. The reaction mixture was concentrated and purified by flash chromatography (Et$_2$O) to give vinylogous urethane Compound 70 (381 mg, 85 percent) as a yellow solid, m.p. =118°-120° C. decomp. (from CH$_2$Cl$_2$); R$_f$ =0.11 (20 percent EtOAc in PhH); [a]$_D^{25}$ = −654° (c 0.29, CH$_2$Cl$_2$); IR (thin film) $v_{max}$ 3425, 3342, 3237 cm$^{-1}$; $^1$H NMR (500 MHz, C$_6$D$_6$) δ 6.41 (s, 1 H, C=CH—CO$_2$), 5.53 (bs, 1 H, NH), 5.44 (d, J =1.7 Hz, 1 H, CH—C≡C), 5.28 (d, J =9.6 Hz, 1 H, CH=CH), 5.15 (dd, J =1.7, 9.6 Hz, 1 H, CH=CH), 4.39 (bs, 1 H, NH), 3.42-3.23 (m, 4 H, ethylene ketal), 2.37 (ABq, J =13.0 Hz, Δv =57 Hz, 2 H, CH$_2$), 1.04 [t, J =8.6 Hz, 9 H, Si(CH$_2$CH$_3$)$_3$], 0.86-0.72 (m, 6 H, Si(CH$_2$CH$_3$)$_3$); FAB HRMS (NBA/CsI) m/e 558.0713, M+Cs+ calcd for C$_{23}$H$_{27}$NO$_5$Si 558.0713.

EXAMPLE 17

Methyl (1'S,5'R)-5',6'-Dihydro-3'-oxo-5'-(triethylsilyl)oxy spiro[1,3-dioxolane-2,7'(3'H)-[1,5][3]hexene[1,5-]diyno[1H-2]benzo pyran]-8'-yl Carbamate (Compound 71)

A solution of Compound 70 (443 mg, 1.042 mmol) in CH$_2$Cl$_2$ (50 mL) at zero degrees C was treated with pyridine (1.30 mL, 16.1 mmol) and triphosgene (936 mg, 3.22 mmol) and stirred at 25° C. for 40 minutes. The solution was then cooled to zero degrees C and treated with pyridine (1.30 mL, 16.1 mmol) and MeOH (9.2 mL, excess) and stirred at zero degrees C for 30 minutes. The solution was poured into brine (50 mL) and extracted with CH$_2$Cl$_2$ (3×50 mL). The combined organic extracts were dried (Na$_2$SO$_4$), concentrated and purified by flash chromatography (70 percent Et$_2$O in petroleum ether) to give carbamate Compound 71 (443 mg, 88 percent) as a white foam; R$_f$ =0.39 (Et$_2$O); [a]$_D^{25}$ = −550° (c 2.9, CH$_2$Cl$_2$); IR (thin film) $v_{max}$ 3293, 1728, 1669 cm$^{-1}$; $^1$H NMR (500 MHz, CDCl$_3$) δ 6.15 (s, 1 H, C=CH—CO2), 6.09 (bs, 1 H, CH—C≡C), 5.98 (bs, 1 H, NH), 5.91 (d, J =9.6 Hz, 1 H, CH=CH), 5.81 (dd, J =1.8, 9.6 Hz, 1 H, CH=CH), 4.20-3.91 (m, 4 H, ethylene ketal), 3.73 (s, 3 H, CO$_2$Me), 2.34 (ABq, J =13.5 Hz, Δv =102 Hz, 2 H, CH$_2$), 0.98 (t, J =9.4 Hz, 9 H, Si(CH$_2$CH$_3$)$_3$), 0.80-0.66 (m, 6 H, Si(CH$_2$CH$_3$)$_3$; $^{13}$C NMR (125 MHz, CDCl$_3$) δ 162.6, 154.4, 154.1, 128.1, 124.7, 124.7, 123.4, 110.8, 104.7, 99.2, 96.3, 90.7, 87.9, 69.2, 68.7, 65.9, 65.3, 53.3, 45.4, 6.9, 5.9; FAB HRMS (NBA/CsI) m/e 616.0760, M+Cs+ calcd for C$_{25}$H$_{29}$NO$_7$Si 616.0768.

EXAMPLE 18

Methyl (1'S,5'R)-5',6'-dihydro-3'-hydroxy-5'-(triethylsilyl)oxyspiro[1,3-dioxolane-2,7'(3'H)-[1,5][3]hexene[1,-5diyno[1H-2]ben zopyran]-8'-yl carbamate (Compound 72ab)

A solution of Compound 71 (57.0 mg, 0.118 mmol) in CH$_2$CL$_2$ (5 mL) at −78° C. was treated with DIBAL (0.35 mL of a 1.0M solution in CH$_2$Cl$_2$, 0.35 mmol) and stirred at −78° C. for 30 minutes. The reaction was quenched at −78° C. with MeOH (0.5 mL added dropwise), the cooling bath was removed, the reaction mixture was diluted with EtOAc (10 mL) and saturated aqueous Rochelle's salt (10 mL) was added. The mixture was stirred vigorously for 30 minutes until the two phases became clear, and the mixture was extracted with EtOAc (3×14 mL). The combined organic extracts were dried (Na$_2$SO$_4$), concentrated and purified by flash chromatography (Et$_2$O) to give the mixed lactols, Compound 72ab, (54.4 mg, 95 percent) as a white solid consisting of a 4:1 mixture of 3'-epimers; m.p. =90°-102° C. (from PhH); R$_f$ =0.34 (Et$_2$O); [a]$_D^{25}$ = −477° (c 0.69, CH$_2$Cl$_2$); IR (thin film) $v_{max}$ 3400, 3315, 1723 cm$^{-1}$; $^1$H NMR (500 MHz, CDCl$_3$) δ6.04–5.51 (m, 6 H), 4.17-3.87 (m, 4 H, ethylene ketal), 3.71 (s, 3 H, CO$_2$Me), 3.20 (bs, 1 H, OH), 2.42-2.23 (m, 2 H, CH$_2$), 1.01-0.97 (m, 9 H, Si(CH$_2$CH$_3$)$_3$), 0.81-0.68 (m, 6 H Si(CH$_2$CH$_3$)$_3$); FAB HRMS (NBA/CsI) m/e 618.0930, M+Cs+ calcd for C$_{25}$H$_{31}$NO$_7$Si 618.0924.

EXAMPLE 19

Methyl (1R, 8S, 13E)-8-hydroxy-13(2-hydroxyethylidene)-1-(triethylsilyl)oxyspiro[bicyclo[7.3.1]tri deca-4,9-diene-2,6-diyne-11,2'-[1,3]dioxolan]-10-yl carbamate (Compound 73)

A solution of the mixed lactols, Compound 72ab, (54.4 mg, 0.112 mmol) in MeOH 93 mL) was treated at zero degrees C with NaBH$_4$ (64 mg, 1.7 mmol) and stirred at zero degrees C until complete consumption of Compound 72ab had occurred (about one hour). The reaction was quenched by the dropwise addition of AcOH (1 mL) and H$_2$O (4 drops) at zero degrees C. The mixture was stirred for five minutes and then concentrated. THF (1 mL), MeOH (2 mL) and H$_2$O (2 drops) were added to the residue and stirred for 15 minutes. The mixture was poured into saturated sodium bicarbonate solution (15 mL) and extracted with CH$_2$Cl$_2$ (3×20 mL). The combined organic layers were dried (Na$_2$SO$_4$), concentrated and purified by flash chromatography (Et$_2$O) to give diol Compound 73 (43.2 mg, 88 percent) as a colorless oil; R$_f$ =0.16 (Et$_2$O); [a]$_D^{25}$ = −221° (c 1.7, CH$_2$Cl$_2$); IR (thin film) $v_{max}$ 3362 (bs), 1718 cm$^{-1}$; $^1$H NMR (500 MHz, CDCl$_3$) δ 6.41 (bs, 1 H, NH), 6.28 (dd, J =6.4, 7.6, 1 H, C=CH—CH$_2$), 5.85 (d, J =9.5 Hz, 1 H, CH=CH), 5.79 (dd, J =1.5, 9.5 Hz, 1 H, CH=CH), 5.67 (bs, 1 H, CH—C≡C), 4.63 (bs, 1 H, OH), 4.28 (dd, J =7.6, 13.7 Hz, 1 H, CHH—OH), 4.19 (dd, J =6.4, 13.7 Hz, 1 H, CHH—OH), 3.99-3.87 (m, 4 H, ethylene ketal), 3.73 (s, 3 H, CO$_2$Me), 2.33 (ABq, J =13.6 Hz, Δv =173 Hz, CH$_2$), 0.97 (t, J =7.8 Hz, 9 H, Si(CH$_2$CH$_3$)$_3$), 0.80-0.68 (m, 6 H, Si(CH$_2$CH$_3$)$_3$); FAB HRMS (NBA/CsI) m/e 620.1086, M+Cs+ calcd for C$_{25}$H$_{33}$NO$_7$Si 620.1081.

EXAMPLE 20

Methyl (1R, 8S, 13E)-1,8-di(triethylsilyl)oxy-13-(2-trimethyl acetoxyethylidene)spiro[bicyclo[7.3.1]tri deca-4,9-diene-2,6-diyne-11,2'-[1,3]dioxolan]-10-yl carbamate (Compound 74)

A solution of diol Compound 73 (48.2 mg, 99.0 mmol) in CH$_2$Cl$_2$ (1 mL) was treated at 25° C. with pyridine (120 mL, 1.5 mmol) and pivaloyl chloride (36 mL, 0.30 mmol) and stirred for four hours. The solution was then cooled to zero degrees C and triethylsilyl trifluoromethanesulfonate (67 mL, 0.30 mmol) was added. The solution was stirred 10 minutes, poured into brine (15 mL) and extracted with $CH_2Cl_2$ (3×15 mL). The combined organic extracts were dried ($Na_2SO_4$), concentrated and purified by flash chromatography (50 percent $Et_2O$ in petroleum ether) to give Compound 74 (45.2 mg, 67 percent) as a colorless oil; $R_f$=0.21 (50 percent $Et_2O$ in petroleum ether); $[a]_D^{25}$ = −162° (c 2.7, $CH_2Cl_2$); IR (thin film) $\nu_{max}$ 3334, 1737, 1728 cm$^{-1}$; $^1$H NMR (500 MHz, $CDCl_3$) δ 6.03 (dd, J =2.7, 8.9 Hz, 1 H, C=CH—$CH_2$), 5.85 (bs, 1 H, NH), 5.85 (d, J =9.5 Hz, 1 H, CH=CH), 5.76 (dd, J =1.7, 9.5 Hz, 1 H, CH=CH), 5.75 (d, J =1.7 Hz, 1 H, CH—C≡C), 4.96 (bd, J =14.1 Hz, 1 H, CHH—OPiv), 4.58 (dd, J =8.9, 14.1 Hz, CHH—OPiv), 4.10-3.82 (m, 4 H, ethylene ketal), 3.70 (s, 3 H, $CO_2Me$), 2.28 (ABq, J =13.3 Hz, Δν =180 Hz, $CH_2$), 1.17 (s, 9 H, $^t$Bu), 0.96 (t, J =7.7 Hz, 18 H, 2× Si($CH_2CH_3$)$_3$), 0.78-0.67 (m, 12 H, 2× Si($CH_2CH_3$)$_3$); FAB HRMS (NBA/CsI) m/e 818.2505, M+Cs+ calcd for $C_{36}H_{55}NO_8Si_2$ 818.2521.

EXAMPLE 21

Methyl (1R, 8S, 13E)-1,8-Di(triethylsilyl)oxy-13-(2-hydroxy ethylidene)spiro[bicyclo[7.3.1]trideca-4,9-diene-2,6-diyne-11,2'-[1,3]dioxolan]-10-yl carbamate (Compound 75)

A solution of pivaloate Compound 74 (45.2 mg, 66.0 mmol) in $CH_2Cl_2$ (3 mL) at −78° C. was treated with DIBAL (0.20 mL of a 1.0M solution in $CH_2Cl_2$, 0.20 mmol) and stirred for one hour. The reaction mixture was quenched at −78° C. with MeOH (0.5 mL added dropwise), the cooling bath was removed, the reaction mixture was diluted with EtOAc (10 mL) and saturated aqueous Rocheele's salt (10 mL) was added. The mixture was vigorously stirred for 30 minutes until the two phases became clear, poured into brine (15 mL) and extracted with EtOAc (3×20 mL). The combined organic extracts were dried ($Na_2SO_4$), concentrated and purified by flash chromatography (70 percent $Et_2O$ in petroleum ether) to give alcohol Compound 75 (33.2 mg, 84 percent) as a colorless oil; $R_f$=0.17 (70 percent $Et_2O$ in petroleum ether); $[a]_D^{25}$ = −193° (c 1.8, $CH_2Cl_2$); IR (thin film) $\nu_{max}$ 3400, 1731 cm$^{-1}$; $^1$H NMR (500 MHz, $CDCl_3$) δ 6.21 (t, J =6.6 Hz, 1 H, C=CH—$CH_2$), 5.90 (bs, 1 H, NH), 5.87 (d, J =9.4 Hz, 1 H, CH=CH), 5.78 (bs, 1 H, CH—C≡C), 5.76 (dd, J =1.5, 9.4 Hz, 1 H, CH=CH), 4.21 (t, J =6.6 Hz, 2 H, $CH_2$—OH), 4.07-3.82 (m, 4 H, ethylene ketal), 3.70 (s, 3 H, $CO_2Me$), 2.29 (ABq, J =13.5 Hz, Δν= 195 Hz, 2 H, $CH_2$), 0.97 (t, J =8.1 Hz, 18 H, 2× Si($CH_2CH_3$)$_3$), 0.79-0.68 (m, 12 H, 2× Si($CH_2CH_3$)$_3$); FAB HRMS (NBA/CsI) m/e 734.1945, M+Cs+ calcd for $C_{31}H_{47}NO_7Si_2$ 734.1945.

EXAMPLE 22

Methyl (1R, 8S, 13E)-13-[2-(acetylthio)ethylidene]-1,8-di(tri ethylsilyl)oxyspiro[bicyclo[7.3.1]trideca-4,9-diene-2,6-diyne-11,2'-[1,3]dioxolan]-10-yl carbamate (Compound 76)

A solution of triphenylphosphine (145 mg, 0.55 mmol) in THF (2 mL) at zero degrees C wa treated with diethylazodicarboxylate (70 mL, 0.44 mmol) and stirred at zero degrees C for 30 minutes. AcSH (31 mL, 0.44 mmol) was added followed by alcohol Compound 76 (33.2 mg, 55.2 mmol) in THF (1 mL +0.5 mL washing) and the solution was stirred at zero degrees C for 30 minutes. The solution was poured into saturated sodium bicarbonate solution (20 mL) and extracted with $CH_2Cl_2$ (3×20 mL). The combined organic layers were dried ($Na_2SO_4$), concentrated and purified by flash chromatography (30 percent $Et_2O$ in petroleum ether) to give thioacetate 89 (33.8 mg, 93 percent) as a colorless oil; $R_f$=0.18 (50 percent $Et_2O$ in petroleum ether); $[a]_D^{25}$ = −96° (c 0.59, $CH_2Cl_2$); IR (thin film) $\nu_{max}$ 3314, 1729, 1692 cm$^{-1}$; $^1$H NMR (500 MHz, $CDCl_3$) δ 6.70 (bs, 1 H, NH), 5.97 (dd, J =6.2, 9.4 Hz, 1 H, C=CH—$CH_2$), 5.76 (dd, J =1.4, 9.2 Hz, 1 H, CH=CH), 4.08-3.76 (m, 6 H, $CH_2$-S and ethylene ketal), 3.71 (s, 3 H, $CO_2Me$), 2.30 (s, 3 H, SAc), 2.25 (ABq, J =13.1 Hz, Δν =204 Hz, 2 H, $CH_2$), 0.98-0.94 (m, 18 H, 2× Si($CH_2CH_3$)$_3$), 0.73-0.68 (m, 12 H, 2× SiCH$_2CH_3$)$_3$); FAB HRMS (NBA/CsI) m/e 792.1839, M+Cs+ calcd for $C_{33}H_{49}NO_7Si_2S$ 792.1823.

EXAMPLE 23

Methyl (1R, 8S, 13E)-1,8-Di(triethylsilyl)oxy-13-[2-(methyltri thio)ethylidene]spiro[bicyclo[7.3.1]tride ca-4,9-diene-2,6-diyne-11,2'-[1,3]dioxolan]-10-yl carbamate (Compound 78)

A solution of thioacetate Compound 76 (18.7 mg, 28.4 mmol) in $CH_2Cl_2$ (2 mL) at −78° C. was treated with DIBAL (0.14 mL of a 1.0M solution in $CH_2Cl_2$, 0.14 mmol) and stirred at −78° C. for 30 minutes. The reaction mixture was quenched at −78° C. with MeOH (0.5 mL added dropwise), the cooling bath was removed and the reaction mixture was diluted with EtOAc (10 mL). Saturated aqueous Rochelle's salt (10 mL) was added and the mixture was vigorously stirred for 30 minutes until the two phases became clear. The mixture was extracted with EtOAc (3×15 mL), the combined organic extracts were dried ($Na_2SO_4$) and concentrated to give crude thiol Compound 77.

The crude thiol Compound 77 was dissolved in $CH_2Cl_2$ (2 mL) at zero degrees C and N-(methyldithio)phthalimide (32 mg, 0.14 mmol) was added. The solution was stirred 30 minutes at zero degrees C and then applied directly to a flash chromatography column and eluted with 30 percent $Et_2O$ in petroleum ether to give trisulfide Compound 78 (14.0 mg, 71 percent) as a colorless oil; $R_f$ = −100° (c 0.49, $CH_2Cl_2$); IR (thin film) $\nu_{max}$ 3285, 1738 cm$^{-1}$; $^1$H NMR (500 MHzm $CDCl_3$) δ 6.22 (dd, J =4.9, 10.3 Hz, 1 H, C=CH—$CH_2$), 5.94 (bs, 1 H, CH=CH), 4.10-3.63 (m, 6 H, $CH_2$S and ethylene ketal), 3.70 (s, 3 H, $CO_2Me$), 2.53 (s, 3 H, SSSMe), 2.33 (ABq, J =13.3 Hz, Δν=140 Hz, 2 H, $CH_2$), 1.00–0.95 (m, 18 H, 2× Si($CH_2CH_3$)$_3$), 0.75-0.67 (m, 12 H, 2× Si($CH_2CH_3$)$_3$); FAB HRMS (NBA/CsI) m/e 828.1355, M+Cs+ calcd for $C_{32}H_{49}NO_6Si_2S_3$ 828.1315.

EXAMPLE 24

(−)-Calicheamicinone (Compound 2)

A solution of Compound 78 (14.0 mg, 20.1 mmol) in THF (1 mL) and $H_2O$ (4 drops) was treated with TsOH (5 mg) and stirred at 25° C. for 16 hours. The reaction mixture was diluted with petroleum ether (2 mL) and dichloromethane (2 mL) and applied to a flash chromatography column eluting with 50 percent $Et_2O$ in petroleum ether to give (−)-calicheamicinone (Compound 2; 5.6 mg, 66 percent) as a colorless gum; $R_f$ =0.30 (70 percent $Et_2O$ in petroleum ether); $[a]_D^{25}$ = −472° (c 0.21, $CH_2Cl_2$); IR (thin film) $\nu_{max}$ 3340, 1711, 1672 cm$^{-1}$; $^1$H NMR (500 MHz, $CDCl_3$) δ 6.92 (bs, 1 H, NH), 6.47 (dd, J =6.4, 9.2 Hz, 1 H, C=CH—$CH_2$), 6.00

(bs, 1 H, CH—C≡C), 5.90 (dd, J =1.3, 9.4 Hz, 1 H, CH=CH), 5.87 (d, J =9.4 Hz, 1 H, CH=CH), 4.09 (dd, J =9.2, 14.1 Hz, 1 H, CHHS), 3.84 (dd, J =6.4, 14.1 Hz, 1 H, CHHS), 3.77 (s, 3 H, $CO_2Me$), 3.32 (bs, 1 H, OH), 3.01 (ABq, J =17.1 Hz, $\Delta\nu$ =180 Hz, 2 H, $CH_2$), 2.83 (bs, 1 H, OH); $^{13}C$ NMR (125 MHz, $CDCl_3$) $\delta$ 191.2, 154.6, 137.4, 130.5, 126.2, 124.4, 123.8, 100.2, 99.9, 87.9, 84.8, 72.6, 64.6, 53.5, 52.3, 38.7, 22.6 (1 olefinic signal hidden); FAB HRMS (NBA/CsI) m/e 555.9323, $M+Cs^+$ calcd for $C_{18}H_{17}NO_5S_3$ 555.9323.

EXAMPLE 25

Sulfurodamine B Cytotoxicity Assay

Cytotoxicity assays using (−)-calicheamicinone were carried out as follows:

1. Preparation of target cells in 96-well plates
a. Drain media from $T_{75}$ flask of target cell line(s) and carefully wash cell monolayer two times with sterile PBS (approximately 5 mL per wash)
b. Add 5 mL trypsin/EDTA solution and wash monolayer for approximately 15 seconds
c. Drain all but approximately 1 mL of trypsin/EDTA from flask, cap flask tightly, and incubate at 37° C. for approximately two to five minutes until cells come loose.
d. Add 10–15 mL tissue culture (T.C.) medium (RPMI 1640 plus 10 percent fetal calf serum and 2 mM L-glutathione to flask and pipet gently up and down to wash cells.
e. Remove a ½ mL aliquot of the cell suspension and transfer to a glass 12×75 mm culture tube for counting.
f. Count cells on a hemacytometer using trypan blue, and determine percent viability.
g. Adjust volume of cell suspension with T.C. media to give a density of $1\times10^5$ cells/mL.
h. Add 100 μL of T.C. medium to wells A1 and B1 of a 96-well plate for blanks.
i. Add 100 μL of cell suspension to the remaining wells of the 96-well plates.
j. Incubate plates for 24 hours at 37° C., 5–10 percent $CO_2$ in a humidified incubator.

2, Preparation of sample drugs and toxic control
a. Stock drug solutions were prepared by dissolving drug in the appropriate solvent (determined during chemical characterization studies) and sterile filtering the drug-solvent solution through a sterile 0.2 μ filter unit. An aliquot was taken from each filtered drug solution and the O.D. was measured to determine the drug concentration.
b. Dilute the stock drug solution prepared above with T.C. medium to the desired initial concentration ($10^{-2}$–$10^{-4}$M). A minimum volume of 220 μL of diluted drug is required per 96-well plate used in the assay.
c. Prepare toxic control by diluting stock doxorubicin solution to $10^{-7}$ to $10^{-9}$M in T.C. medium. A minimum volume of 300 μL is required per 96-well plate.

3. Addition of Sample Drugs, Compounds, Chimeras and Controls to 96-well Plates
a. Remove and discard 100 μL of T.C. medium from the wells in Column #2 of the 96-well plate using a multichannel pipettor and sterile tips.
b. Add 100 μL of the initial compound dilution to adjacent duplicate wells in Columns #2. (Four materials can be tested in duplicate per 96-well plate.)
c. Remove 10 μL of diluted compound from the wells in Column #2 and transfer to the corresponding wells in Column #3. Mix by pipetting up and down gently approximately five times.
d. Transfer 10 μL to the appropriate wells in Column #4 and continue to make 1:10 dilutions of compound across the plate through Column #12.
e. Remove and discard 100 μL of medium from wells F1, G1, and H1. Add 100 μL of toxic control (Doxorubicin diluted in T.C. medium) to each of these wells.
f. Incubate (37° C., 5–10 percent $CO_2$ in humidified incubator) plates for a total of 72 hours. Check plates at 24 hour intervals microscopically for signs of cytotoxicity.

4. Cell Fixation
a. Adherent cell lines:
 1. Fix cells by gently layering 25 μL of cold (4° C.) 50 percent trichloroacetic acid (TCA) on top of the growth medium in each well to produce a final TCA concentration of 10 percent.
 2. Incubate plates at 4° C. for one hour.
b. Suspension cell lines:
 1. Allow cells to settle out of solution.
 2. Fix cells by gently layering 25 μL of cold (4° C.) 80 percent TCA on top of the growth medium in each well.
 3. Allow cultures to sit undisturbed for five minutes.
 4. Place cultures in 4° C. refrigerator for one hour.
c. Wash all plates five times with tap water.
d. Air dry plates.

5. Staining Cells
a. Add 100 μL of 0.4 percent (wt./vol.) Sulforhodamine B (SRB) dissolved in 1 percent acetic to each well of 96-well plates using multichannel pipettor.
b. Incubate plates at room temperature for 30 minutes.
c. After the 30 minute incubation, shake plates to remove SRB solution.
d. Wash plates two times with tap water and 1× with 1 percent acetic acid, shaking out the solution after each wash. Blot plates on clean dry absorbent towels after last wash.
e. Air dry plates until no standing moisture is visible.
f. Add 100 μL of 10 mM unbuffered Tris base (ph 10.5) to each well of 96-well plates and incubate for five minutes on an orbital shaker.
g. Read plates on a microtiter plate reader at 540 nM.

$IC_{50}$ values; i.e., the concentration of Compound required to kill one-half of the treated cells, were then calculated.

The cell lines assayed are listed below along with their respective sources:

The $IC_{50}$ values obtained from the above assays were as follows for (−)-calicheamicinone and daunomycin:

| | $IC_{50}$ Values (Molar) Drug | |
|---|---|---|
| Cell Line* | Daunomycin | (−)-Calicheamicinone |
| ATCC Capan-1 (pancreatic carcinoma) | $7.8\times10^{-7}$ | $3.1\times10^{-6}$ |
| CHO (Chinese hampster ovary) | $1.6\times10^{-6}$ | $6.3\times10^{-5}$ |
| H-322 (lung carcinoma) | $1.6\times10^{-6}$ | $2.5\times10^{-5}$ |
| ATCC HL-60 (promyeocytic leukemia) | $2.0\times10^{-7}$ | $2.0\times10^{-7}$ |
| ATCC HT-29 (Colon carcinoma) | $1.6\times10^{-6}$ | $2.8\times10^{-5}$ |
| ATCC MCF-7 (Breast carcinoma) | $3.9\times10^{-7}$ | $1.3\times10^{-5}$ |
| ATCC Molt-4 (T-cell leukemia) | $10^{-10}$ | $10^{-9}$ |
| NHDF (Normal human dermal | $3.9\times10^{-7}$ | $1.3\times10^{-5}$ |

-continued

| Cell Line* | IC$_{50}$ Values (Molar) Drug | |
|---|---|---|
| | Daunomycin | (−)-Cali- cheamicinone |
| fibroblast | | |
| ATCC Ovcar 3 (Ovarian carcinoma) | $3.9 \times 10^{-7}$ | $2.5 \times 10^{-5}$ |
| UCLA-P3 (lung carcinoma) | $1.6 \times 10^{-6}$ | $2.5 \times 10^{-5}$ |
| ATCC P-388 (Mouse leukemia) | $2.0 \times 10^{-7}$ | $3.9 \times 10^{-7}$ |
| ATCC SK-MEL-28 (Melanoma) | $1.6 \times 10^{-6}$ | $2.5 \times 10^{-5}$ |

*Cell lines were obtained from the American Type Culture Collection (ATCC), 12301 Parklawn Drive, Rockville, Maryland, U.S.A. 20852-1776, except as noted hereinafter: UCLA-P3 was obtained from Dr. Ralph Reisfeld of The Scripps Research Institute, La Jolla, California; NHDF cells were obtained from Clonetics Corporation, San Diego, California.

ANALYTICAL DATA

Compound 21

IR (thin film): $\nu_{max}$ =3498, 3411, 1722 cm$^{-1}$; $^1$H NMR (500 MHz, CDCl$_3$) δ: 7.87 (2H, m, phthalimide); 7.70 (2H, m, phthalimide); 6.11 (1H, t, J=6.7 Hz, CH=C); 6.02 (1H, dd, J=9.6, 0.9 Hz, enediyne); 5.87 (1H, dd, J=9.5, 0.6 Hz, enediyne); 5.49 (1H, bd, J=2.9 Hz, CH—OH); 4.39 and 4.41 (2H, ABX quartet, J=1.8 Hz, CH$_2$—OTBS); 3.86 (2H, m, ethylene ketal); 3.70 (2H, m, ethylene ketal); 2.76 and 2.27 (2H, AB quartet, J=13.5 Hz, CH$_2$); 2.31 (1H, bd, J=3.1 Hz, OH); 0.94 and 0.90 (18H, 2s, 2× Si$^t$Bu); and 0.27, 0.23, 0.13, 0.12 (12H, 4s, 4× SiMe); FAB Mass Spectrum (NBA/CsI) m/e 806.1945, M+Cs calcd. for C$_{37}$H$_{47}$NO$_7$Si$_2$ 806.1945.

Compound 57

Compound 57 pale yellow oil; R$_f$=0.31 (silica, 10 percent methanol in dichloromethane), [a]$_D^{25}$= −49.2° (c=0.66, CHCl$_e$); $^1$H NMR, (500 MHz, C$_6$D$_6$); δ =7.56 (d, 2H, J⊙7.6 Hz, Ar), 7.32–7.13 (m, 8H, Ar), 5.88 (bs, 1H, OH), 5.86 (s, 1H, E-1), 5.75 (bs, 1H, O—N—H), 4.99 (d, 1 H, J=11.7 Hz, CH$_2$—Ph), 4.67 (d, 1H, J=11.7 Hz, CH$_2$—Ph), 4.54–4.47 (m, 3H, A-1, CH$_2$-Ph-hydroxylamine), 4.32 (dd, 1H, J=10.8, 9.2 Hz, E-5ax), 4.04 (dd, 1H, J=9.5, 9.5 Hz, A-3), 4.02–3.94 (m, 1H, E-3), 3.90 (dd, 1H, J=10.8, 4.7 Hz, E-5eq), 3.88 (dd, 1H, J=9.5, 7.6 Hz, A-2), 3.57 (dq, 1H, J=9.2, 4.7 Hz, E-4), 2.57–2.42 (m, 3H, E-2eq, N—CH$_2$), 2.34 (dd, 1H, J=9.5, 9.5 Hz, A-4), 1.54 (dd, 1H, J=10.2, 10.2 Hz, E-2ax), 1.36 (d, 3H, J=6.0 Hz, A-6), 0.99 (t, 3H, J=6.5 Hz, N—CH$_2$—CH$_3$); IR (CHCl$_3$): $\nu_{max}$ =2964, 2932, 1456, 1095, 1071 cm$^{-1}$; HRMS calcd. for C$_{28}$H$_{40}$N$_2$O7 (M+Cs•) 649.1890; found 649.1900.

The foregoing is intended as illustrative of the present invention but not limiting. Numerous variations and modifications may be effected without departing from the true spirit and scope of the novel concepts of the invention.

We claim:

1. A compound whose structure corresponds to the formula

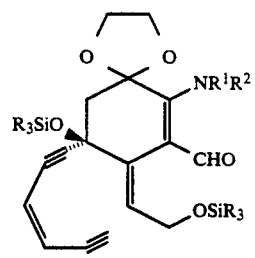

R$^1$ and R$^2$ together form a moiety selected from the group consisting of

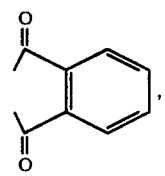,

,

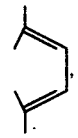,

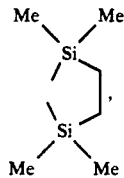,

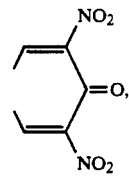,

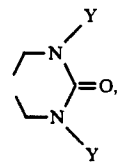,

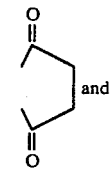 and

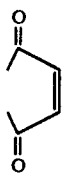

Y is methyl or benzyl;

SiR$_3$ contains three R groups that are the same or different and are C$_1$–C$_6$ alkyl or phenyl.

2. The compound according to claim 1 wherein R$^1$ and R$^2$ together form a phthaloyl group.

3. The compound according to claim 2 wherein SiR$_3$ is t-butyldimethylsilyl.

4. A compound whose structure corresponds to the formula

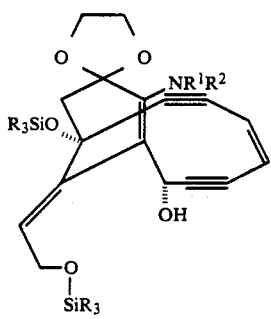

R$^1$ and R$^2$ together form a moiety selected from the group consisting of

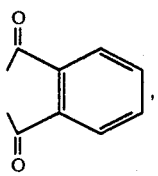

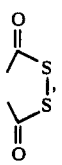

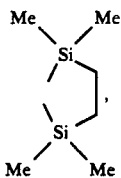

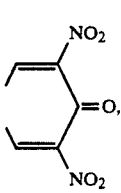

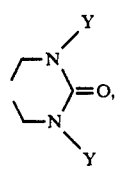

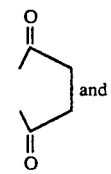 and

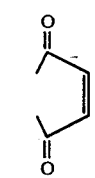

Y is methyl or benzyl; and

SiR$_3$ contains three R groups that are the same or different and are C$_1$–C$_6$ alkyl and phenyl.

5. The compound according to claim 4 wherein R$^1$ and R$^2$ together form a phthaloyl group.

6. The compound according to claim 5 wherein SiR$_3$ is t-butyldimethylsilyl.

* * * * *